(12) United States Patent
Toledano et al.

(10) Patent No.: US 12,029,529 B2
(45) Date of Patent: Jul. 9, 2024

(54) SYSTEM, METHOD AND COMPUTER PRODUCT FOR DIFFERENTIATING BETWEEN TISSUE STATES AND TYPES

(71) Applicant: H.T BIOIMAGING LTD., Ganei Am (IL)

(72) Inventors: Shani Toledano, Givatayim (IL); Moshe Tshuva, Tel-Aviv (IL); Sharon Gat, Bat Hefer (IL)

(73) Assignee: H.T BIOIMAGING LTD., Ganei Am (IL)

( * ) Notice: Subject to any disclaimer, the term of this patent is extended or adjusted under 35 U.S.C. 154(b) by 754 days.

(21) Appl. No.: 17/252,138

(22) PCT Filed: Jun. 12, 2019

(86) PCT No.: PCT/IL2019/050665
§ 371 (c)(1),
(2) Date: Dec. 14, 2020

(87) PCT Pub. No.: WO2019/239410
PCT Pub. Date: Dec. 19, 2019

(65) Prior Publication Data
US 2021/0251492 A1    Aug. 19, 2021

Related U.S. Application Data

(60) Provisional application No. 62/683,836, filed on Jun. 12, 2018.

(51) Int. Cl.
*A61B 5/01*    (2006.01)
*A61B 5/00*    (2006.01)

(52) U.S. Cl.
CPC .......... *A61B 5/015* (2013.01); *A61B 5/0088* (2013.01); *A61B 5/45* (2013.01); *A61B 5/4887* (2013.01);
(Continued)

(58) Field of Classification Search
CPC ......... A61B 5/015; A61B 5/0088; A61B 5/45; A61B 5/4887; A61B 5/7267; A61B 2562/0271
See application file for complete search history.

(56) References Cited

U.S. PATENT DOCUMENTS

| | | | |
|---|---|---|---|
| 7,513,876 B2 | 4/2009 | Casscells et al. | |
| 8,078,262 B2 | 12/2011 | Murphy et al. | |

(Continued)

FOREIGN PATENT DOCUMENTS

| | | |
|---|---|---|
| CN | 112584757 A | 3/2021 |
| FR | 3028116 A1 | 5/2016 |

(Continued)

OTHER PUBLICATIONS

Pirtini Cetingul et al, "Quantitative Evaluation of Skin Lesions Using Transient Thermal Imaging". Proceedings of the 2010 14th International Heat Transfer Conference. 2010 14th International Heat Transfer Conference, vol. 1. Washington, DC, USA. Aug. 8-13, 2010. pp. 31-39. ASME. https://doi.org/10.1115/IHTC14-22465.

(Continued)

*Primary Examiner* — Eric F Winakur
(74) *Attorney, Agent, or Firm* — The Roy Gross Law Firm, LLC; Roy Gross

(57) ABSTRACT

A method for differentiating between tissue states or types including receiving a sequence of thermal data of a tissue, wherein the sequence is sampled at at least one location of the tissue while the tissue is being thermally disturbed, deriving from the thermal data at least one tissue-related thermal variable associated with each of the tissue locations, segmenting the tissue into segments comprising the locations having corresponding the at least one thermal variable and generating an output indicating the tissue segments. The (Continued)

disclosure also includes a system and computer product for differentiating between tissue states or types.

17 Claims, 19 Drawing Sheets

(52) U.S. Cl.
CPC .... *A61B 5/7267* (2013.01); *A61B 2562/0271* (2013.01)

(56) References Cited

U.S. PATENT DOCUMENTS

| | | | |
|---|---|---|---|
| 8,774,902 | B2 | 7/2014 | Dekel et al. |
| 8,864,669 | B2 | 10/2014 | Behar |
| 8,923,954 | B2 | 12/2014 | Herman |
| 2004/0236225 | A1 | 11/2004 | Murphy et al. |
| 2007/0106157 | A1 | 5/2007 | Kaczkowski et al. |
| 2007/0213617 | A1 | 9/2007 | Berman et al. |
| 2010/0222698 | A1 | 9/2010 | Turnquist et al. |
| 2011/0021944 | A1 | 1/2011 | Amon et al. |
| 2011/0066035 | A1 | 3/2011 | Norris et al. |
| 2011/0087096 | A1 | 4/2011 | Behar |
| 2011/0230942 | A1 | 9/2011 | Herman et al. |
| 2011/0297848 | A1 | 12/2011 | Haidekker et al. |
| 2012/0316439 | A1 | 12/2012 | Behar |
| 2013/0116573 | A1 | 5/2013 | Herman |
| 2015/0276491 | A1 | 10/2015 | Rud |
| 2016/0287088 | A1 | 10/2016 | Case et al. |
| 2017/0027450 | A1 | 2/2017 | Toledano et al. |
| 2018/0014734 | A1 | 1/2018 | Rogers et al. |
| 2018/0098727 | A1 | 4/2018 | Spahn et al. |
| 2018/0333105 | A1 | 11/2018 | Hayat et al. |
| 2021/0245201 | A1 | 8/2021 | Toledano et al. |

FOREIGN PATENT DOCUMENTS

| | | |
|---|---|---|
| JP | 2007215809 A | 8/2007 |
| JP | 2017006337 A | 1/2017 |
| WO | 2008039388 A3 | 4/2008 |
| WO | 2015159284 A1 | 10/2015 |
| WO | 2017184201 A1 | 10/2017 |
| WO | 2019239411 A2 | 12/2019 |

OTHER PUBLICATIONS

Becker SM. (2015) Analytical Bioheat Transfer: Solution Development of the Pennes' Model. In Becker S; Kuznetsov A (Ed.), Heat Transfer and Fluid Flow in Biological Processes: 77-124. Amsterdam: Elsevier. http://dx.doi.org/10.1016/B978-0-12-408077-5.00004-3.

Robotics and Autonomous Systems Group CSIRO Data61. (Jun. 17, 2013). HeatWave: 3D Thermography System. YouTube. https://www.youtube.com/watch?v=wZWN1frZ7mo.

3Shape. (Sep. 18, 2015). Insane speed-scanning with 3Shape TRIOS 3 intraoral scanner. YouTube. https://www.youtube.com/watch?v=X5CvIUZ5DpQ.

PCT International Search Report for International Application No. PCT/IL2019/50665, dated Nov. 1, 2019, 3pp.

PCT Written Opinion for International Application No. PCT/IL2019/50665, dated Nov. 1, 2019, 5pp.

PCT International Preliminary Report on Patentability for International Application No. PCT/IL2019/50665, dated Dec. 15, 2020, 6pp.

Kaczmarek M. et al "Optical excitation methods in active dynamic thermography in medical diagnostics", Proc. SPIE 5566, Optical Security and Safety, Aug. 26, 2004, pp. 120-126 https://doi.org/10.1117/12.577220.

Kandlikar S."Infrared imaging technology for breast cancer detection—Current status, protocols and new directions", International Journal of Heat and Mass Transfer, vol. 108, Part B, May 2017, pp. 2303-2320 doi:10.1016/j.ijheatmasstransfer.2017.01.086.

Silva L et al "Hybrid Analysis for Indicating Patients with Breast Cancer using Temperature Time Series", Computer Methods and Programs in Biomedicine, vol. 130, Jul. 2016, pp. 142-153 http://dx.doi.org/10.1016/j.cmpb.2016.03.002.

SYSTEM, METHOD AND COMPUTER PRODUCT FOR DIFFERENTIATING BETWEEN TISSUE STATES AND TYPES

CROSS REFERENCE TO RELATED APPLICATIONS

This application is a National Phase of PCT Patent Application No. PCT/IL2019/050665 having International filing date of Jun. 12, 2019, which claims the benefit of priority under 35 U.S.C. § 119(e) of U.S. Provisional Patent Application No. 62/683,836 filed on Jun. 12, 2018, entitled "SYSTEM, METHOD AND COMPUTER PRODUCT FOR DIFFERENTIAL IDENTIFICATION OF TISSUE TYPES IN SITU".

This application is also related to International Patent Application No. PCT/IL2015/050392 published as PCT Publication No. WO2015/159284, entitled "A DEVICE AND METHOD FOR CANCER DETECTION, DIAGNOSIS AND TREATMENT GUIDANCE USING ACTIVE THERMAL IMAGING" to the same inventors. The contents of the above applications are all incorporated by reference as if fully set forth herein in their entirety.

FIELD OF THE INVENTION

The present invention, in some embodiments thereof, relates to thermal data collecting systems, methods and computer products.

BACKGROUND

Thermography is a field in which thermal radiation such as Infra-Red radiation emitted from an object is detected by a sensor (e.g., thermographic camera) that converts the sensed thermal radiation into an image (thermogram). A thermogram allows to observe differences in the thermal radiation emitted from various areas over the surface of the imaged object.

Thermal radiation emitted from an object without external thermal intervention—passive thermography—can be higher or lower than the background thermal radiation emitted. Passive thermography has many applications such as surveillance of people against a background and medical diagnosis (specifically thermology).

Unlike in passive thermography, an energy source may actively heat an object—active thermography—to produce a thermal contrast between the object and the background. Active thermography is used in cases in which the inspected object is in equilibrium with the surroundings.

The foregoing examples of the related art and limitations related therewith are intended to be illustrative and not exclusive. Other limitations of the related art will become apparent to those of skill in the art upon a reading of the specification and a study of the figures.

SUMMARY

The following embodiments and aspects thereof are described and illustrated in conjunction with systems, tools and methods which are meant to be exemplary and illustrative, not limiting in scope.

According to an aspect in accordance with some embodiments of the invention, there is provided a method for differentiating between tissue states or types including receiving a sequence of thermal data of a tissue, wherein the sequence is sampled at at least one location of the tissue while the tissue is being thermally disturbed, deriving from the thermal data at least one thermal variable associated with each of the tissue locations, segmenting the tissue into segments including the locations having corresponding the at least one thermal variable, and generating an output indicating the tissue segments.

According to some embodiments, the thermal data is received from at least one of thermal imaging, infrared (IR) sensor, mercury thermometer, resistance thermometer, thermistor, thermocouple, semiconductor-based temperature sensor, pyrometer, gas thermometer, laser thermometer and ultrasound. In some embodiments, the thermal data is received by thermal imaging, and wherein the location includes a pixel or a voxel of an image. In some embodiments, the at least one thermal variable is selected from the group consisting of: tissue organism metabolic heat source, heat loss due to blood perfusion, blood temperature, tissue density, specific heat, tissue thermal conductivity factor, tissue thermal conductivity coefficient, tissue thermal conductivity surface area, tissue surface temperature, and time-dependent thermal gradient between tissue and ambient temperature.

In some embodiments, the at least one thermal variable further includes at least one of ambient temperature and a heat source temperature. In some embodiments, the thermal disturbing includes at least one of: actively effecting a change in temperature in at least a portion of the tissue from an initial temperature to an end temperature, actively effecting a change in temperature in at least a portion of the tissue for a specified period of time, passively allowing a change in temperature in at least a portion of the tissue from an initial temperature to an end temperature, and passively allowing a change in temperature in at least a portion of the tissue for a specified period of time.

According to some embodiments, the method includes extracting a set of features based on at least some of the thermal data and thermal variables, wherein the features are selected from groups of features including: features representing various derivative values of the variables, features representing noise in the variables, features based on decay equations, features based on Fourier series and correlative features based on a variance of the features. In some embodiments, the segmenting is further based on the locations having a corresponding set of features. In some embodiments, the correspondence is determined, based, at least in part, on a variance value of all the variables and the features not exceeding a specified threshold. In some embodiments, the method further includes determining a tissue state or type associated with each of the segments, based, at least in part, on correlating the at least one thermal variable with predefined values of the thermal variables associated with a plurality of tissue states or types. In some embodiments, the correlating further includes correlating the features.

In some embodiments, the deriving, segmenting, extracting, and determining is performed by a machine learning classifier trained, at a training stage, on a training set including a plurality of thermal data sequences, each sampled at at least one location of a tissue, while the tissue is being thermally disturbed, and labels associated with a state or type of the at least one location.

In some embodiments, the method further includes applying, at an inference stage, the trained machine learning classifier to at least one target thermal data sequence sampled at a location of a tissue, while the tissue is being thermally disturbed, to determine a state or type of the tissue location.

According to an aspect in accordance with some embodiments of the invention, there is provided a computer program product including a non-transitory computer-readable storage medium having program code embodied therewith, the program code executable by at least one hardware processor to receive a sequence of thermal data of a tissue, wherein the sequence is sampled at at least one location of the tissue while the tissue is being thermally disturbed, derive from the thermal data at least one tissue-related thermal variable associated with each of the tissue locations, segment the tissue into segments including the locations having corresponding the at least one thermal variable, and generate an output indicating the tissue segments. In some embodiments, the at least one thermal variable indicates a state or type of the tissue.

In some embodiments, the thermal data is received from at least one of thermal imaging, infrared (IR) sensor, mercury thermometer, resistance thermometer, thermistor, thermocouple, semiconductor-based temperature sensor, pyrometer, gas thermometer, laser thermometer and ultrasound. In some embodiments, the thermal data is received by thermal imaging and wherein the location includes a pixel or a voxel. In some embodiments, the thermally disturbed tissue includes actively or passively effecting a change in temperature on at least a portion of the tissue from an initial temperature to an end temperature.

In some embodiments, the thermally disturbed tissue includes effecting a change in temperature on at least a portion of the tissue over at least one predetermined period of time. In some embodiments, the at least one tissue-related thermal variable includes at least one intrinsic tissue thermal parameter affecting thermal behavior of the cell. In some embodiments, the computer program product is configured to calculate a set of features based on at least some of the thermal data and thermal variables.

In some embodiments, the features are selected from groups of features including features representing various derivative values of the variables, features representing noise in the variables, features based on decay equations, features based on Fourier series and correlative features based on a variance of the features. In some embodiments, the segmenting is further based on the locations having a corresponding set of features.

In some embodiments, the correspondence is determined, based at least in part on a variance value of all the variables and the features not exceeding a specified threshold. In some embodiments, the deriving includes calculating a set of thermal features of each of the tissue locations based, at least in part, on the at least one thermal variable.

According to an aspect in accordance with some embodiments of the invention, there is provided a system, including a thermal sensor configured to sample a sequence of thermal data from at at least one location on tissue while the tissue is being thermally disturbed, and a processor configured to derive from the thermal data at least one tissue-related thermal variable associated with each of the tissue locations, segment the tissue into segments including the locations having corresponding the at least one thermal variable, and generate an output indicating the tissue segments, wherein the system includes a heating or cooling source directed at at least the surface of tissue and configured to actively heat or cool the tissue.

In some embodiments, the at least one thermal variable indicates a state or type of the tissue. In some embodiments, the thermal data is received from at least one of thermal imaging, infrared (IR) sensor, mercury thermometer, resistance thermometer, thermistor, thermocouple, semiconductor-based temperature sensor, pyrometer, gas thermometer, laser thermometer and ultrasound. In some embodiments, the thermal data is received by thermal imaging and wherein the location includes a pixel or a voxel.

In some embodiments, the thermally disturbed tissue includes actively or passively effecting a change in temperature on at least a portion of the tissue from an initial temperature to an end temperature. In some embodiments, the thermally disturbed tissue includes effecting a change in temperature on at least a portion of the tissue over at least one predetermined period of time. In some embodiments, the at least one tissue-related thermal variable includes at least one intrinsic tissue thermal parameter affecting thermal behavior of the cell.

In some embodiments, thermal data and thermal variables. In some embodiments, the features are selected from groups of features including features representing various derivative values of the variables, features representing noise in the variables, features based on decay equations, features based on Fourier series and correlative features based on a variance of the features. In some embodiments, the segmenting is further based on the locations having a corresponding set of features.

In addition to the exemplary aspects and embodiments described above, further aspects and embodiments will become apparent by reference to the figures and by study of the following detailed description.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. The figures are listed below.

DETAILED DESCRIPTION

Figure 1:
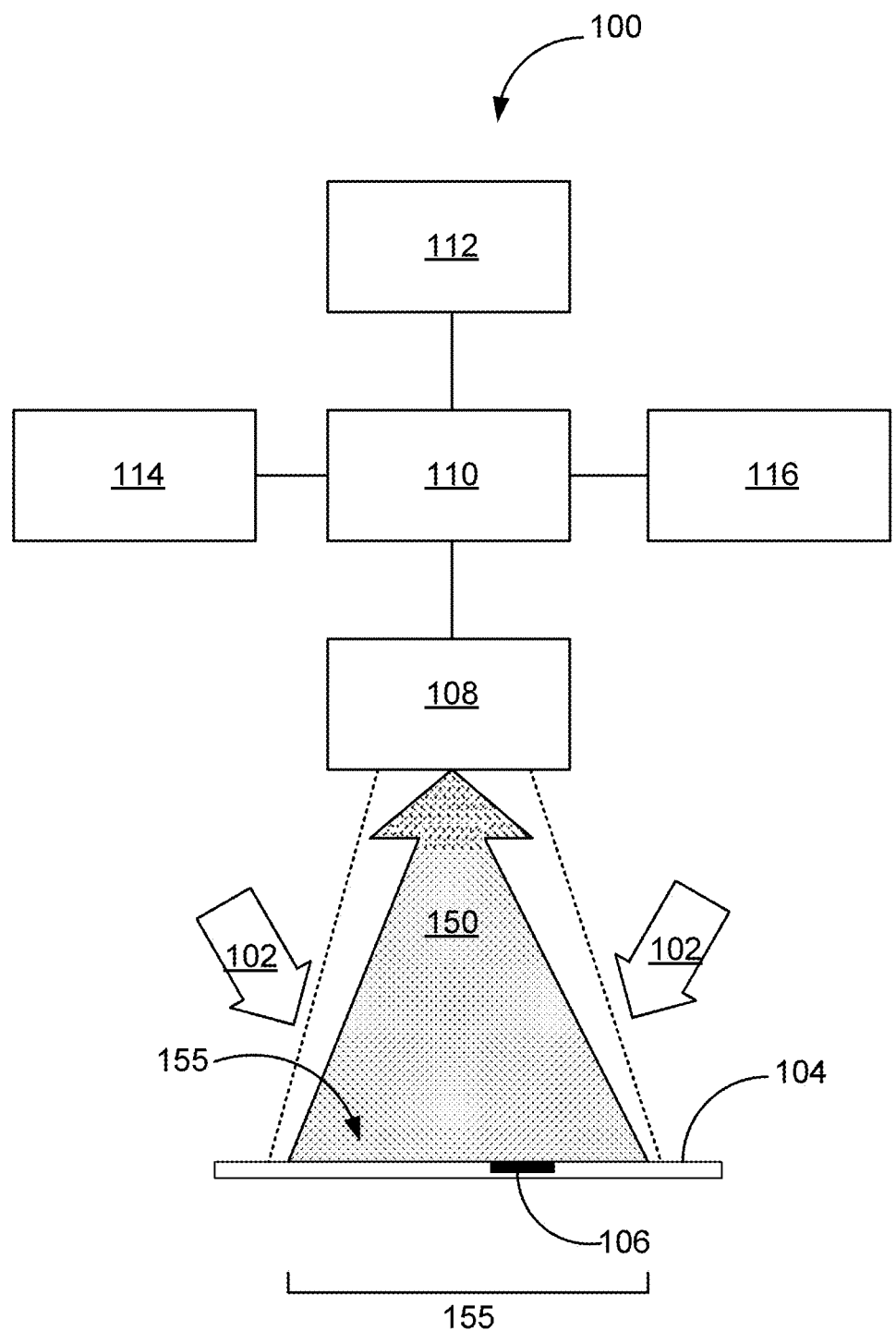
FIG. 1. is a simplified diagram of a thermal imaging system for differentiation and/or identification of tissue states or types in accordance with some embodiments of the present invention.

According to an aspect of some embodiments of the present invention, there is provided a method for differentiation between one or more tissue locations or regions, based, at least in part, on thermal properties associated with these locations or regions calculated from thermal data. In some embodiments, the thermal data is collected from at least one location on the tissue. In some embodiments, the method comprises collecting a temporal sequence of thermal data for the at least one location, while concurrently effecting a thermal change in the tissue.

The term "tissue" as used herein includes any bodily or bodily-related matter such as soft tissue, hard tissue and cellular and non-cellular matter e.g., muscle, bone, teeth and/or bacteria.

In some embodiments, the present disclosure provides for differentiating between states and/or types of tissue. In some embodiments, tissue types include, but are not limited to, muscle, bone, neural tissue, blood vessels, glandular tissue and/or adipose tissue.

In some embodiments, tissue states include, but are not limited to, tissue clinical states e.g., normal tissue, inflamed tissue, tissue neoplasm, tissue dysplasia, Mucocele, fibroma, fibroepithelial polyp, pathological tissue, precancerous tissue, and/or cancerous tissue.

Though tissue thermal data can be sampled by many sensing devices, e.g., infrared (IR) sensors, mercury thermometers, resistance thermometers, thermistors, thermocouples, semiconductor-based temperature sensors, pyrometers, gas thermometers, laser thermometers and ultrasound, for the purpose of clarity and simplicity, by way of example but not by way of limitation, hereafter, determination of a state of one or more tissue locations is demonstrated based on thermal properties calculated from data received by thermal imaging.

According to an aspect of some embodiments in accordance with the invention, there is provided a method for differentiating between tissues according to tissue states or types, based, at least in part, on effecting a change in temperature of at least a surface of at least a portion of a tissue. For example, in some embodiments, effecting a temperature change comprises heating at least a surface of at least a portion of a tissue, from an initial, base temperature over a predetermined first period of time e.g., $t_0$ to $t_1$ followed by allowing the temperature of the tissue to passively return (e.g., cool) to the base temperature, over a second period of time e.g., $t_1$ to $t_2$.

In some embodiments, during the combined first and second periods of time $t_0$ to $t_2$, a sequence of thermal data, e.g. thermal images (e.g., a video stream), of at least the surface of the tissue is obtained using one or more suitable thermal imaging devices, e.g., an infrared (IR), near infrared (NIR), short-wave infrared (SWIR), and/or another imaging device. In some embodiments, additional images and/or image streams may be obtained during at least a portion of the time period $t_1$ to $t_2$. In some embodiments, the additional images may comprise red-green-blue (RGB) images, monochrome images, ultraviolet (UV) images, multi-spectral images, and/or hyperspectral images.

In some embodiments, image data are processed to extract a plurality of values associated with at least some of the pixels in each image. In some embodiments, certain portion of the values may be extracted at a point in time and/or as a time series over part or all of the period $t_0$ to $t_2$.

In some embodiments, one or more values may be translated into one or more feature vectors, including a plurality of time-dependent feature vectors. In some embodiments, the one or more feature vectors may be compared with predetermined features or feature vectors associated with one or more tissue states or types. In some embodiments, a state of one or more regions of the tissue may be determined, based, at least in part, on the comparison.

In some embodiments, the one or more feature vectors for each pixel are grouped into one or more groups indicating the groups as regions of tissue states or types of the imaged tissue.

In some embodiments, the present disclosure provides for an output which indicates the tissue states or types of one or more regions of a thermal-imaged tissue. In some embodiments, the output may comprise an image comprising a graphical representation of one or more regions, based, at least in part, on the identified tissue state or type associated with each region. For example, in some embodiments, the boundaries of each region may be demarcated, and/or part or the whole of the region may be presented using one or more color schemes. In some embodiments, the graphical representation may be generated as a thermal image, an RGB image, and/or another and/or a different type of image. In some embodiments, the boundaries of the identified tissue states or types are mapped on a tissue state distribution map. In some embodiments, the boundaries of the identified tissue states or types are mapped in the form of a graph, such as, for example, a histogram.

In some embodiments, a machine learning classifier may be trained on a dataset comprising feature vector sets associated with a plurality of subject tissues, wherein the training dataset may be labelled with one or more tissue states or types present in the several regions of the subject tissues. In some embodiments, a trained classifier of the present disclosure may then be applied to a target feature set from a target subject, to determine the presence of the one or more physiological or pathological parameters in the target tissue.

In some embodiments, the actively changing the temperature of tissue comprises actively heating or actively or passively cooling the portion of tissue during at least a portion of the imaging period of time.

In some embodiments, the processing or analysis is performed for each pixel of the obtained image. In some embodiments, the analysis includes extracting a plurality of pixel-level values for each pixel, that represent a quantification of a physiological or pathological parameter.

In some embodiments, the method comprises receiving a sequence of thermal data of a tissue, wherein the sequence is sampled at one or more locations of the tissue while the tissue is being thermally disturbed, deriving from the thermal data at least one tissue-related thermal variable associated with each of the tissue locations, segmenting the tissue into segments comprising the locations having corresponding one or more of the thermal variable and generating an output indicating the tissue segments.

In some embodiments, the method comprises calculating a set of features based on at least some of the thermal data and thermal variables, in which case the segmenting is based on locations having a corresponding set of features. In some embodiments, the correspondence is determined, based at least in part on a variance value of all of the variables and the features not exceeding a specified threshold. In some embodiments, the method comprises calculating a set of thermal features of each of the tissue locations based, at least in part, on the one or more thermal variables. In some embodiments, the one or more thermal variables indicate a state or type of the tissue. In some embodiments, the features are selected from groups of features including features representing various derivative values of the variables, features representing noise in the variables, features based on decay equations, features based on Fourier series and correlative features based on a variance of the features.

In some embodiments, the method comprises acquiring a sequence of thermal images over a period of time. In some embodiments, extracting pixel values from the thermal images, for each pixel and/or point of measurement, generating feature vectors representing tissue cell thermal properties over the period of time, clustering pixels having similar features and reflecting the pixel clusters onto corresponding regions in the imaged tissue. In some embodiments, the method comprises determining a tissue state or type of at least one of the regions based on comparing the features to known feature sets of tissue states or types. In some embodiments, the method comprises generating an output e.g., a graphic representation of the tissue state in one or more of the regions. In some embodiments, the method comprises using trained machine learning classifiers to classify a state of tissue in each region. In some embodiments, generating feature vectors is optional and the method comprises determining a tissue state or type of at least one of the regions based on comparing the features to known feature sets of tissue states or types.

In some embodiments, the method includes generating a map representing distribution of the thermal variables and/or thermal features over the portion of tissue within the imaged field of view (FOV). In some embodiments, the method includes analyzing the distribution over the map of pixel-level values and identifying clusters of values each cluster being within a same pixel value range and associated the identified values with a specific tissue type or state. In some embodiments, clusters of pixels in the thermal image sharing a same value are associated with corresponding clusters of specific tissue cell types.

In some embodiments, the distribution analysis of the pixel-level values is based on calculation of variance between the calculated pixel-level values.

In some embodiments, the method includes generating a plurality of pixel-level values distribution maps, each associated with a specific physiological or pathological parameter. In some embodiments, a plurality of maps generated from obtained pixel-level values are combined or superimposed to enhance identification of clusters of tissue cell types.

According to an aspect of some embodiments of the present invention there is provided a method for differentiating between states or types of tissue. In some embodiments, the method includes obtaining pixel-level values from a thermal image of at least a portion of tissue within a thermal imager field of view (FOV). In some embodiments, the method comprises actively changing a temperature of a portion of tissue over a set period of time. In some embodiments, the method includes obtaining the thermal images (frames) of the tissue during the temperature change. In some embodiments, the method includes processing consecutive frames of obtained pixel-level values and extracting pixel-level values regarding a change within a set period of time in one or more variables or features derived from the pixel-level values representing physiological or pathological parameters associated with the tissue.

In some embodiments, the method includes generating a graph for each pixel representing the change in the pixel-level values, thermal variables or features derived from the pixel-level values during the tissue temperature change. In some embodiments, the method includes processing e.g., by performing a comparative analysis of one or more portions of graph curves and identifying groups of pixels having similar or same curve patterns associated with a specific tissue state or type. In some embodiments, the identified pixel groups sharing the same pixel-level values, variables or features are associated with a specific type or state of tissue. In some embodiments, the distribution analysis of the pixel-level values, variables or features is based on calculation of variance between the graph curves based on the values obtained from each pixel.

In some embodiments, the method comprises actively heating the tissue and allowing the tissue to cool passively. In some embodiments, processing of imaging frames obtained during the period of active heating and passive cooling is expressed by a graph curve having a growth portion, a peak and a decay portion. In some embodiments, a thermal imaging system comprises a processor and a computer program product configured to execute the comparative analysis on the growth portion only of the resulting curve. In some embodiments, the comparative analysis is executed only on the decay portion of the resulting curve. In some embodiments, the computer program product of the processor is configured to execute the comparative analysis on the curve peak temperature only at the meeting point of the growth portion and the decay portion of the resulting curve.

Figure 2A:
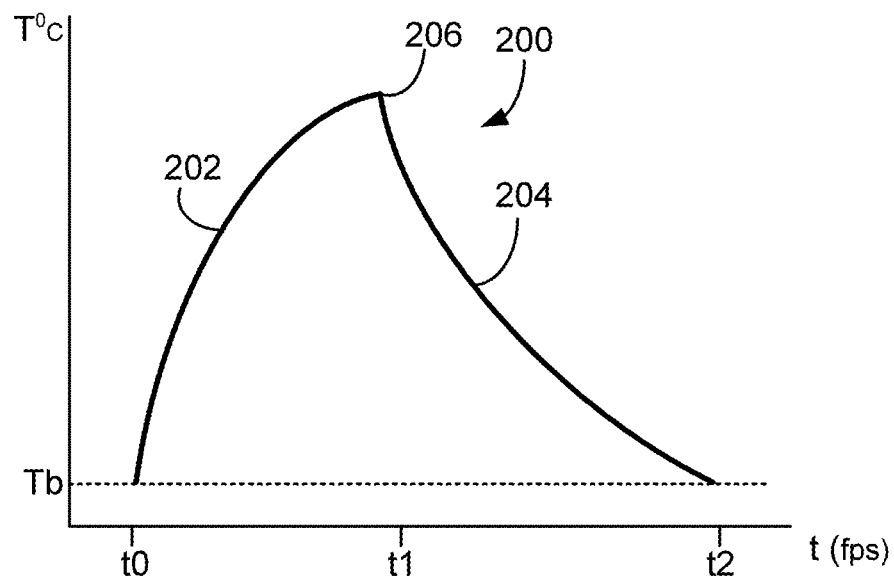
FIGS. 2A and 2B are graphs of thermal curves associated with biothermal behavior 7 of tissue cells under temperature variation in accordance with some embodiments of the invention.
Figure 2B:
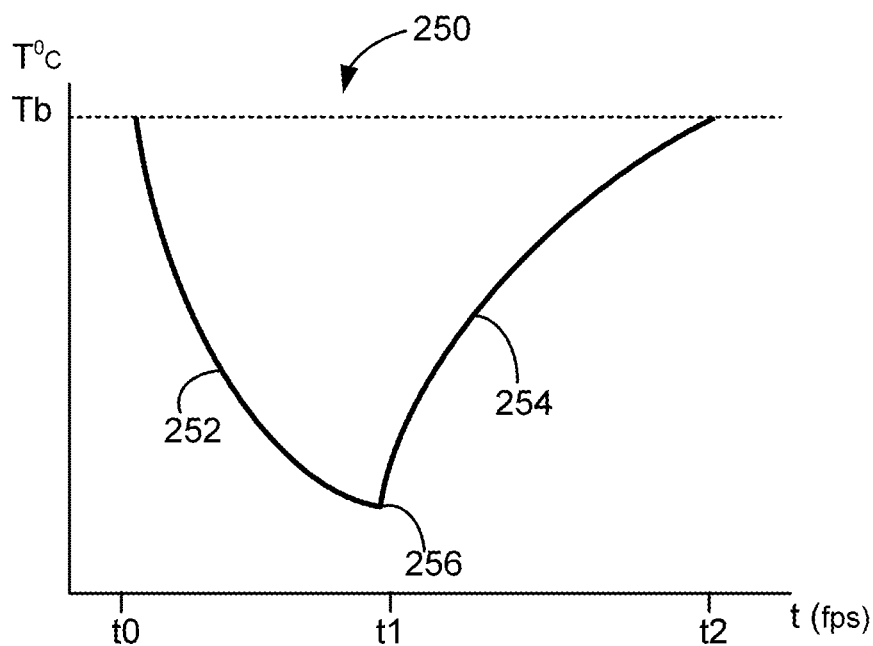

Alternatively, and optionally in some embodiments, and as shown, for example, in FIG. 2B, the method comprises actively cooling the tissue and allowing the tissue to warm up passively. In some embodiments, analysis of imaging frames obtained during the period of active cooling and passive warming is expressed by a graph curve having a decay portion, a trough (minimum point) and a growth portion. In some embodiments, a thermal imaging system comprises a processor and a computer program product configured to execute the comparative analysis on the growth portion only of the resulting curve. In some embodiments, the comparative analysis is executed only on the decay portion of the resulting curve. In some embodiments, the computer program product of the processor is configured to execute the comparative analysis on the curve trough (minimum temperature) only at the meeting point of the growth portion and the decay portion of the resulting curve.

In some embodiments, the method includes processing by performing a comparative analysis of the variance in seasonal noise for curves from each pixel and identifying clusters of pixels having similar curve seasonal noise associated with a tissue state or type. In some embodiments, the identified clusters are associated with tissue cell clusters.

In some embodiments, the method includes generating a plurality of distribution maps, each based on generated pixel-level values associated with a specific physiological parameter. In some embodiments, a plurality of generated maps are combined or superimposed to enhance identification of states or types of tissue cell clusters.

In some embodiments, the method includes incrementally actively heating or cooling the portion of tissue. In some embodiments, the method includes obtaining thermal images (frames) over a set period of time. In some embodiments, the method includes processing consecutive frames of the image obtained during each actively heating or cooling increment and extracting pixel-level values regarding a change within the heating increment in one or more physiological or pathological parameters associated with the tissue.

According to an aspect of some embodiments of the present invention there is provided a method for differentiating between states or types of tissue. In some embodiments, the method includes actively heating the tissue. In some embodiments, heating the tissue includes applying a line-shaped beam of heating energy (e.g., Infrared light) to one side of the tissue that heats a strip of tissue. In some embodiment, the method includes obtaining the thermal images (frames) of the portion of tissue within the FOV of a thermal imager over a set period of time.

Alternatively, and optionally, in some embodiments the method for differentiating between states or types of tissue includes actively cooling the tissue. In some embodiments, cooling the tissue includes applying a line-shaped beam of cooling energy (e.g., sprays or contact coolant) to one side of the tissue that cools a strip of tissue. In some embodiment, the method includes obtaining the thermal images (frames) of the portion of tissue within the FOV of a thermal imager over a set period of time.

In some embodiments, the method includes processing consecutive frames of the image obtained over the period of time and extracting pixel-level values regarding a rate of thermal diffusion in a direction perpendicular to the vector beam and/or the heated strip of tissue during the set period of time. In some embodiments, processing consecutive frames of the image obtained over the set period of time includes associating the pixel-level values regarding the rate of thermal diffusion in the tissue with one or more physiological or pathological parameters associated with the tissue. In some embodiments, the method includes identifying clusters of pixels sharing pixel-level values or variable or features based on the pixel-level values associated with a diffusion rate within a given range of diffusion rates that is associated with a tissue type or state. In some embodiments, the identified clusters of pixels are associated with corresponding clusters of cells of a specific tissue type or state on a graphic representation of the imaged tissue.

According to an aspect of some embodiments of the present invention there is provided a method for differentiating between states or types of tissue. In some embodiments, the method includes heating the tissue. In some embodiments, heating the tissue includes applying heating energy (e.g., Infrared light) to arbitrary portions of the tissue surface. Alternatively, and optionally in some embodiments, the method includes actively cooling the tissue. In some embodiments, cooling the tissue includes applying cooling energy (e.g., sprays or contact coolants) to arbitrary portions of the tissue surface. In some embodiment, the method includes obtaining the thermal image of the portion of tissue within the FOV of a thermal imager over a set period of time.

In some embodiments, the method includes processing consecutive frames of thermal images (frames) obtained over the period of time and extracting pixel-level values regarding a rate of thermal diffusion over the surface of the tissue during the set period of time. In some embodiments, processing consecutive frames of the image obtained over the set period of time includes associating the information regarding the rate of thermal diffusion in the tissue with one or more physiological or pathological parameters associated with the tissue. In some embodiments, the method includes identifying clusters of pixels sharing a diffusion rate within a given range that is associated with a tissue type. In some embodiments, the identified clusters are associated with corresponding clusters of cells of a specific tissue type on a graphic representation of the imaged tissue.

According to an aspect of some embodiments of the present invention there is provided a method for differentiating between states or types of tissue. In some embodiments, the method includes heating the tissue. In some embodiments, heating the tissue includes applying heating energy (e.g., Infrared light) to a predetermined depth within the tissue. In some embodiment, the method includes obtaining the thermal image of the portion of tissue at various depths between the tissue surface and the predetermined depth over a set period of time.

Alternatively, and optionally, in some embodiments the method for differentiating between states or types of tissue includes actively cooling the tissue. In some embodiments, cooling the tissue includes applying cooling energy (e.g., sprays or contact coolant) to a predetermined depth within the tissue. In some embodiment, the method includes obtaining thermal images (frames) of the portion of tissue at various depths between the tissue surface and the predetermined depth over a set period of time.

In some embodiments, the method includes processing consecutive frames of the thermal image obtained at any specific depth over the period of time and extracting pixel-level values regarding a rate of thermal diffusion throughout a layer of tissue at the specific depth during the set period of time. In some embodiments, processing consecutive frames of the image obtained over the set period of time includes associating the pixel-level values associated with the rate of thermal diffusion within the tissue with one or more physiological or pathological parameters associated with a tissue. In some embodiments, the method includes identifying clusters of voxels sharing a diffusion rate within a given range that is associated with a specific tissue type or state. In some embodiments, the identified clusters of pixels are associated with corresponding clusters of cells of a specific tissue type or state on a graphic representation of the imaged tissue.

According to an aspect of some embodiments of the present invention there is provided a computer program product comprising a non-transitory computer-readable storage medium having program code embodied therewith, the program code executable by at least one hardware processor to process one or more thermal images (frames) of a portion of tissue within a field of view (FOV) of a thermal imager.

In some embodiments, the computer program product is executable to calculate from information received from each pixel of an obtained image. In some embodiments, the program product is executable to calculate a pixel-level value associated with a physiological or pathological parameter of the tissue. In some embodiments, the program product is executable to generate a map based on the calculated values associated with the physiological or pathological parameter of the tissue. In some embodiments, the program product is executable to indicate clusters of pixels having values associated with parameters within a given range of parameters associated with a specific tissue type or state.

In some embodiments, the computer program product is executable to calculate a series of variables and/or features based on pixel-level values received from at least one pixel over a set period of time and associated with a change in physiological or pathological parameters of the tissue. In some embodiments, the program product is executable to calculate the variables and/or features from a plurality of image frames taken over the set period of time. In some embodiments, the program product is executable to generate a curve based on the calculated variable and/or features associated with the change in the physiological or pathological parameter of the tissue over the set period of time. In some embodiments, the program product is executable to indicate clusters of pixels having similar curves and associated with the variance in parameters within a given range or above a given threshold associated with a specific tissue type or state.

The System

Reference is now made to FIG. 1. Which is a simplified diagram of a thermal imaging system for differentiation and/or identification of tissue states or types in accordance with some embodiments of the present invention. In some embodiments, thermal imaging system 100 for differentiation and/or identification of tissue states or types comprises a thermal imager 108 that images a surface of a tissue 104 as it is actively heated or cooled. In some embodiments, thermal imager 108 is in communication with a processor 110. Thermal imaging system 100 processor 110 is configured to process and process thermal images obtained by thermal imager 108 and generate an output map, for example, on a display 112.

In some embodiments, the output map comprises a graphic representation of the calculated pixel-level values. In some embodiments, the output map comprises a graphic representation of the calculated pixel-level values superimposed over an RGB image or any other graphic representation of the imaged tissue. In some embodiments, the output map comprises a graphic representation of calculated variances of the calculated pixel-level values in respect to values of a gold standard. In some embodiments, the output map comprises a graphic representation of the calculated variances in pixel-level values superimposed over an RGB image or any other graphic representation of the imaged tissue.

As illustrated in FIG. 1, a thermal imaging system 100 for differentiation and/or identification of tissue states or types comprises a heating/cooling source 102 directed at a surface of a tissue 104 to be processed. Surface of tissue 104 can be a surface of any tissue or organ in a body e.g., skin, liver, spleen, kidney and urinary bladder. In the embodiment depicted in FIG. 1, surface of tissue 104 comprises cluster of cells of aberrant tissue an aberrant tissue 106.

In some embodiments, active heating can include one or more heating method selected from a cluster of heating methods including radiation, convection and conduction. Heat source 102 can be for example, any suitable heat source such as, for example, High Radiant Flux Density 400 nm Violet LED Emitter LZP-DOUB00-00U5 manufactured by LED Engin®, Inc., San Jose CA 95134, USA or any InfraRed (IR), Radio Frequency (RF), Ultrasound (US), Fluid flow over the surface of the tissue, heating pipes or other carriers, etc.

In some embodiments, active cooling can be applied for example, by evaporation (e.g., alcohol sprays), local coolant sprays (nitrogen), cooling fluid flow over the surface of the tissue, cooling pipes or other carriers, etc.

In some embodiments and as shown in FIG. 1, system 100 digital thermal imager 108 images thermal radiation 150 emitted from the surface of a segment of tissue 104. In some embodiments, imager 108 is a video thermal imager configured to generate consecutive frames of thermal images obtained from the surface of tissue 104 within a field of view (FOV) 155 of thermal imager 108 over a set period of time. In some embodiments, thermal imager 108 comprises a digital microscope thermal imager 108. In some embodiments, thermal imager 108 can be any suitable digital imager such as, for example, a PI 450 Thermal Infrared Video Camera by Optris®, Portsmouth, NH 03801 USA. In some embodiments, system 100 comprises a visible light camera. In some embodiments, digital imager 108 comprises any suitable thermal sensor for example, Mill, Ultrasound, Thermocouple or any other sensor that measures temperature.

In some embodiments and as explained in greater detail elsewhere herein, system 100 comprises a source of illumination 114 that illuminates the tissue and demarcates surgical borders for removal of a cluster of cells of aberrant tissue. In some embodiments and as explained in greater detail elsewhere herein, system 100 comprises a source of ablative energy 116 to ablate the demarcated cluster of cells of aberrant tissue. In some embodiments, source of illumination 114 and source of ablative energy 116 are generated from a single source (e.g., laser).

Processing of Data Obtained from a Single Pixel in a Thermal Image (Frame)

For simplicity of explanation the examples hereinbelow refer to an IR digital imager. However, as explained elsewhere herein, any other suitable thermal imager or sensor can be used.

In some embodiments, digital thermal imager 108 comprises one or more pixel arrays. The pixel arrays react to IR radiation emitted from the imaged surface of tissue 104. One or more pixels react to IR radiation emitted from a corresponding segment ($S_p$) of the imaged surface of tissue 104 within a FOV of the pixel (FOVp). In some embodiments, heat source 102 is configured to gradually actively heat surface of tissue 104 over a set period of time after which active heating is stopped and the tissue is allowed to passively cool during which time the tissue temperature returns to the temperature prior to initiation of the active heating. Throughout the heating and cooling period of time, thermal imager 108 obtains a series of consecutive frames of a thermal image of surface of tissue 104. In some embodiments, each consecutive thermal frame in the obtained series of thermal images is time-stamped and therefore a series of two or more frames obtained over a period of time provides information regarding changes in recorded thermal parameters of the tissue. In some embodiments, system 100 comprises a processor 110 configured to process the recorded thermal parameters and map a thermal behavior of the tissue. In some embodiments and as explained in greater detail elsewhere herein, processor 110 is configured to define a tissue type or state of the imaged tissue based on the thermal behavior map of the imaged tissue.

In some embodiments, cooling source 102 is configured to gradually actively cool surface of tissue 104 over a set period of time after which active cooling is stopped and the tissue is allowed to passively warm up during which time the tissue temperature returns to the temperature prior to initiation of the active cooling. Throughout the cooling and warming up period of time, thermal imager 108 obtains a series of consecutive frames of a thermal image of surface of tissue 104.

In some embodiments, each consecutive thermal frame in the obtained series of thermal images is time-stamped and therefore a series of two or more frames obtained over a period of time provides information regarding changes in recorded thermal parameters of the tissue. In some embodiments, system 100 comprises a processor 110 configured to process the recorded thermal parameters and map a thermal behavior of the tissue. In some embodiments and as explained in greater detail elsewhere herein, processor 110 is configured to define a tissue type or state of the imaged tissue based on the thermal behavior map of the imaged tissue.

In some embodiments, Thermal imaging system 100 processor 110 comprises a non-transitory computer-readable storage medium having program product embodied therewith. The program product is executable by thermal imaging system 100 processor 110 to process e.g., compare and map differences e.g., variance, between consecutive time-stamped frames expressed by variance between different pixel-level values exhibited in at least a portion of tissue within the FOV of a plurality of pixels.

Thermal imaging system 100 processor 110 is configured to process pixel-level values received from each pixel for each consecutive image frame in accordance with the time stamp of each frame and generate a graph obtained from pixel-level values indicating a change in the IR radiation emitted from each location $S_p$ on the surface of tissue 104 over the set period of time. The received data represent a raster graphic pixel value and/or a time-dependent vector pixel value of one or more tissue physiological or pathological parameters at one or more specific points in time.

In some embodiments, one or more tissue physiological or pathological parameters are at least any one of external parameters affecting thermal behavior of the cell e.g., environmental temperature, external heat source and interior and the time-dependent thermal gradient between environment and object and/or intrinsic tissue parameters affecting thermal behavior of the cell (thermal parameters) e.g., tissue and/or organism metabolic heat source, heat loss due to blood perfusion, blood temperature, tissue density, specific heat, thermal conductivity factor, thermal conductivity coefficient, the thermal conductivity surface area (m2), the temperature of the object's surface and the such.

In some embodiments, thermal imaging system 100 processor 110 uses one or more algorithms that use various mathematical expressions to approximate the obtained results to the values received from one or more of the imager pixels and generate pixel-level values based variables and/or features that can be mapped to generate an accurate map of the imaged tissue type/s or state/s.

In some embodiments, for example, calculated pixel-level value-based features are expressed by mathematical expressions. For illustrative purposes only, in one example, a pixel-level value (i.e., temperature at the pixel at a given time) is expressed by the following mathematical expression, which is based on Pennes' equation of bio-thermal conductivity:

$$T(t) = a + be^{ct} + dt$$

wherein (dt) may be normalized by time and variables (a), (b), (c) and (d) are variables derived from Pennes' biothermal conductivity equation which is a widely accepted temperature profiling equation for biological tissues. Variables (a), (b), (c) and (d) are used herein for the purpose of clarity and simplicity, by way of example but not by way of limitation, and can include any number or combination of variables and be any type. For example, variables (a), (b), (c) and (d) can be at least any one of external parameters affecting thermal behavior of the cell e.g., environmental temperature, external heat source and interior and the time-dependent thermal gradient between environment and object and/or intrinsic tissue parameters affecting thermal behavior of the cell (thermal parameters) e.g., tissue and/or organism metabolic heat source, heat loss due to blood perfusion, blood temperature, tissue density, specific heat, thermal conductivity factor, thermal conductivity coefficient, the thermal conductivity surface area (m2) and the temperature of the object's surface.

In some embodiments, a plurality of features may be calculated based, at least in part, on the variables (e.g., variables a, b, c and d), including, but not limited to, features representing various derivative values of the variables, features representing noise in the variables, features based on decay equations, features based on Fourier series, as well as correlative features based on the variance of the features.

The following expression comprises an example for such a derivation based on Pennes' equation expressed as:

$$\rho c_p \frac{\partial T}{\partial t} = \frac{\partial k}{\partial x}\frac{\partial T}{\partial x} + k\frac{\partial^2 T}{\partial x^2} + \frac{\partial k}{\partial y}\frac{\partial T}{\partial y} + k\frac{\partial^2 T}{\partial y^2} + \frac{\partial k}{\partial z}\frac{\partial T}{\partial z} + k\frac{\partial^2 T}{\partial z^2} - \rho c \omega (T - T_a) + g(x, t)$$

In some embodiments, the following assumptions are taken:

a) That the lateral contributions and/or the heat generation are negligible (metabolism time scale is one minute [1]) and therefore obtain the following expression:

$$\rho c_p \frac{\partial T}{\partial t} \approx \frac{\partial k}{\partial z}\frac{\partial T}{\partial z} + k\frac{\partial^2 T}{\partial z^2} - \rho c \omega (T - T_a)$$

b) that $$\frac{\partial k}{\partial z}\frac{\partial T}{\partial z} + k\frac{\partial^2 T}{\partial z^2} \approx$$

$$hC(T - T_{env}) - k\frac{T(z) - T(z - \Delta z)}{(\Delta z)^2} \approx hC(T - T_{env}) - kf(t)(T - T_c)$$

where C is area and (h) is the heat transfer coefficient, Tc is the core temperature, and c) We assume that f(t) changes slowly with time.
Under the disclosed assumptions:

$$\rho c_p \frac{\partial T}{\partial t} \approx hC(T - T_{env}) - kf(t)(T - T_c) - \rho c \omega (T - T_a),$$

-continued
$$\frac{\partial T}{\partial t} \approx \frac{hC - kf(t) - \rho c\omega}{\rho c_\rho} T + \frac{-hCT_{env} + kf(t)T_c + \rho c\omega T_a}{\rho c_\rho},$$

$$\frac{\partial T}{\partial t} \approx -cT + Ac,$$

Where $$c \approx -\frac{hC - kf(t) - \rho c\omega}{\rho c_\rho}, \quad A \approx \frac{-hCT_{env} + kf(t)T_c + \rho c\omega T_a}{hC - kf(t) - \rho c\omega}, \quad B \approx T_i - A$$

Equation (4.65) in Analytical Bioheat Transfer: Solution Development of the Pennes' Model, Sid M. Becker, Chapter 4 agrees with this formulation in the limit 4αt=12; 1→0.

T (t~=0) may also be approximated with a linear function or a higher order polynomial:

$$T(t\approx 0) \approx B + A - cBt = T_i - cBt$$

T(t) is expressed as an exponent for short periods of time (e.g., (t) may be between 0 and 40 seconds, 10 and 30 seconds, 15 and 25 seconds or any number of seconds in between).

In another example and in some embodiments, variable (a) may express initial conditions at the point of transfer from active heating/cooling to passive cooling down or warming of imaged tissue and is not time dependent. In some embodiments, variables (b) and/or (c) express a combination of tissue physiological or pathological parameters such as, for example, density (ρ), specific heat (C) and thermal conductivity (K).

As explained in greater detail elsewhere herein, in some embodiments, extracted variables (a), (b), (c), (d) and other contributing variables, clusters of the same variable or clusters of variables from one or more thermal images together with one or a combination of mathematical expressions are processed by a computer program product of processor 110, using data mining processes, e.g., to cross-reference data, perform data cleansing, and generate an output in a form of a map indicating and/or identifying various tissue states or types within the imaged tissue area.

In some embodiments, the following are alternative exemplary expressions are used for bodies not having an internal heat source:

1. $T(r) = a + be^{-ct}$

2. $\frac{T(t) - T_i}{T\infty - T_i} = 1 - e^{-ct}\left[1 - \frac{2}{\pi} * \left(\sqrt{c} * \sqrt{t} - \frac{1}{3} * c^{\frac{3}{2}} * t^{\frac{3}{2}} + \frac{1}{10} * c^{\frac{5}{2}} * t^{\frac{5}{2}}\right)\right]$ Wherein:
Ti is initial temperature of the body.
T∞ is ambient temperature.
Parameter $$C = \frac{h^2 \cdot \alpha}{k^2}\left[\frac{1}{s}\right]$$

Where—

$$h\left[\frac{w}{m^2 \cdot k}\right]$$

is convective thermal conductivity.

$$k\left[\frac{w}{m \cdot k}\right]$$

is thermal conductivity.

3.

$$\theta(t) = \frac{T(t) - T_{ambient}}{T_i - T_{ambient}} = b * e^{-ct}$$

(With normalize temperatures).

In some embodiments, the following are alternative exemplary expressions are used for bodies having an internal heat source:

1. $T(t) = a + be^{-ct} - dt$

2. $T(t) = a + be^{-ct} - de^{-ht^2}$

3. $T(t) = a + be^{-ct} * de^{-ht^2}$

4. $T(t) = a + be^{-ct} - de^{-gt} \cdot e^{-ht^2}$

Wherein (h) is a convection factor (e.g., transfer of heat from tissue to air) and is therefore dependent on ambient temperature.

In some embodiments, a computer program product of processor 110 is configured to compare one or more potential output maps based on each obtained image to a gold standard and elect to at least one of: adjust the analysis process (e.g., by changing selected variables, selected mathematical calculation combinations and other mathematical and/or statistical manipulations), generate an output map expressing variance between obtained data and the data of the gold standard or not generate an output map if no variance exists.

Graph curves in FIGS. 2A, 2B, 3, 4, 5A, 5B, 5C, 9B, 12, 14A, 14B and 15 represent temperature ($T^0c$) changes over time (t) measured in Image Frames per Second (FPS). For example, in cases in which images are obtained at a rate of 25 FPS, every 25 frames represent one second.

Reference is now made to FIGS. 2A and 2B, which are graphs of thermal curves associated with biothermal behavior of heated tissue in accordance with some embodiments of the invention. In some embodiments, curve 200 exhibits a change in temperature (T) of cells from a base temperature (Tb) within a segment of tissue (Sp) based on IR radiation emitted from each Sp on the surface of tissue 104 over the set period of time (t0 to t1). In some embodiments, curve 200 expresses biothermal behavior of tissue in response to heating over a set period of time (t0 to t1) and comprises a growth portion 202 in response to heating, a decay portion 204 during a cooling period of time (t1 to t2) and a peak temperature 206 at the meeting point (t1) of growth portion 202 and decay portion 204. As is explained in greater detail elsewhere herein, the set period of time ($t_0$ to $t_n$) need not necessary reflect a period of heating followed by a period of cooling and may be broken down into periods of time comprising various modalities of temperature change.

As explained in International Patent Application No. PCT/IL2015/050392 to the same inventors, various states or types of tissues exhibit specific biothermal behavior expressed by one or more of a specific growth portion 202, a specific decay portion 204 and a specific curve peak temperature 206. In some embodiments, the thermal imaging system 100 images the tissue over a total period of time (t0 to t2) and processes data received from the pixel for each consecutive frame of the image in accordance with the time stamp of each frame and generates a growth portion 202 specific for the imaged tissue.

Similarly, in some embodiments, thermal imaging system 100 processes the data received from the pixel for each consecutive frame of the image in accordance with the time stamp of each frame and generates a decay portion 204 specific for the imaged tissue. Accordingly, thermal imaging system 100 can combine specific growth portion 202 and decay portion 204, calculate a meeting point of curve portions 202 and 204 and generate values for each pixel expressing the position of peak temperature 206 on the generated curve 200.

As disclosed elsewhere herein, in some embodiments, the method implemented via system 100 comprises actively changing the temperature of tissue during at least a portion of the imaging period of time (e.g., t0 to t1). In some embodiments, obtained frames provide information regarding changing tissue physiological or pathological parameters over the imaging period of time. In some embodiments, actively changing the temperature of tissue comprises actively heating or actively cooling the portion of tissue during at least a portion of the imaging period of time.

In some embodiments, data can be extracted, as explained elsewhere herein, from at least portions of both active heating and active cooling sessions thus increasing the accuracy of the output maps generated by computer program product of processor 110.

For simplicity of explanation the examples hereinbelow refer only to method embodiments comprising heating followed by cooling. However, all disclosed method embodiments, can be implemented in the same manner replacing active heating with active cooling, e.g., cooling followed by heating.

In some embodiments, the curve 200 generated by thermal imaging system 100 processor 110 is a curve generated from values obtained from a single thermal image pixel over a set period of time e.g., from a set of consecutive thermal images taken over the set period of time. In some embodiments, the generated curve represents a thermal signature of a specific imaged tissue type or state. In an exemplary embodiment shown in FIG. 3, which is a graph of a thermal curve associated with biothermal response of heated tissue in accordance with some embodiments of the invention, a pair of thermal response graphs obtained from two pixels P1 and P2 are compared by being drawn on the same T/t coordinate system.

Figure 3:
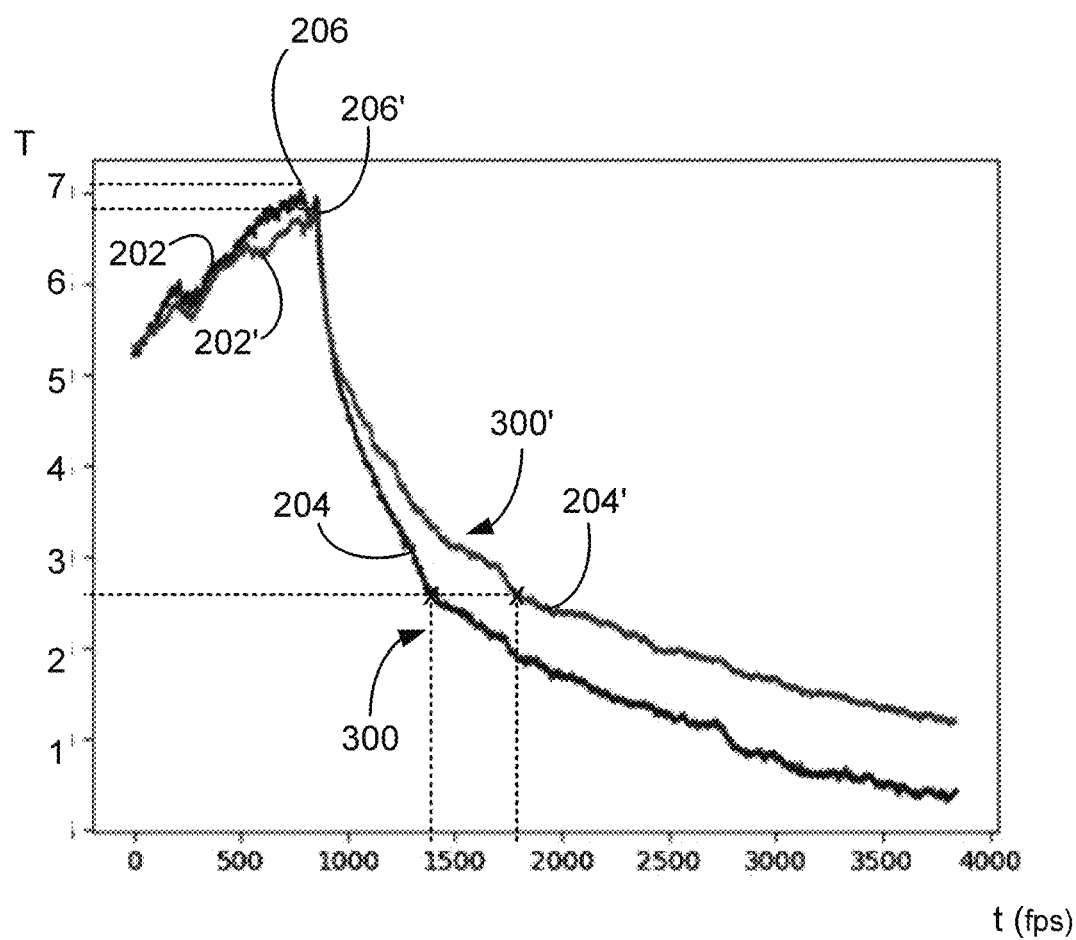
FIG. 3 a graph of a thermal curve associated with biothermal behavior of tissue cells under temperature variation in accordance with some embodiments of the invention.

As depicted in FIG. 3, curve 300, obtained from pixel P1 grows steeply in respect to curve 300' obtained from pixel P2 and arrives at peak temperature 206 earlier than curve 300' peak 206'. Peak temperature 206 is also at a higher temperature (e.g., 45.05° C.) in reference to peak temperature 206' (e.g., 44.90° C.) of curve 300'. The variance between curves 300 and 300' is also exhibited in the decay portions 204 and 204' wherein decay portion 204 of curve 300 us steeper in respect to decay portion 204' of curve 300' arriving, for example, at a temperature of approximately 44° C. after about 1400 sec in reference to decay portion 204' which arrives at the same temperature after about 1750 sec. For simplicity of explanation and in order not to be bound by any examples, the temperature (T) in the graphs depicted in the drawings are scaled by consecutive natural numbers.

Similar to a thermal signature derived from the variance between thermal behavior curves of various tissue states or types, a shape of a thermal behavior curve leading to a peak temperature 206/206' and decaying therefrom also varies between thermal behavior curves and can be identified by thermal imaging system 100 processor 110 as associated with a specific tissue type or state. In some embodiments, thermal imaging system 100 processor 110 processes values received from at least a portion of an array of pixels as explained in greater detail elsewhere herein and manipulate the values to generate an indication of tissue states or types in the imaged tissue.

Accordingly, in some embodiments, thermal imaging system 100 can identify thermal behavior curves 300 and 300' as specific to one or more tissue states or types and can therefore be used to generate an output indicative of the different tissue states or types in the imaged tissue. In some embodiments, outputs from thermal imaging system 100 processor 110 can be compiled into a lookup table associating a thermal signature derived from a thermal behavior graph with a specific tissue type or state that can be separately identified and verified histologically.

As disclosed elsewhere herein, the variances are exhibited all along the thermal behavior curve and therefore enable processing portions of variable length (timeframes) of the curve such as only growing portion 202, only decay portion 204, only by peak temperature 206 location or any portions or combination thereof.

Figure 4:
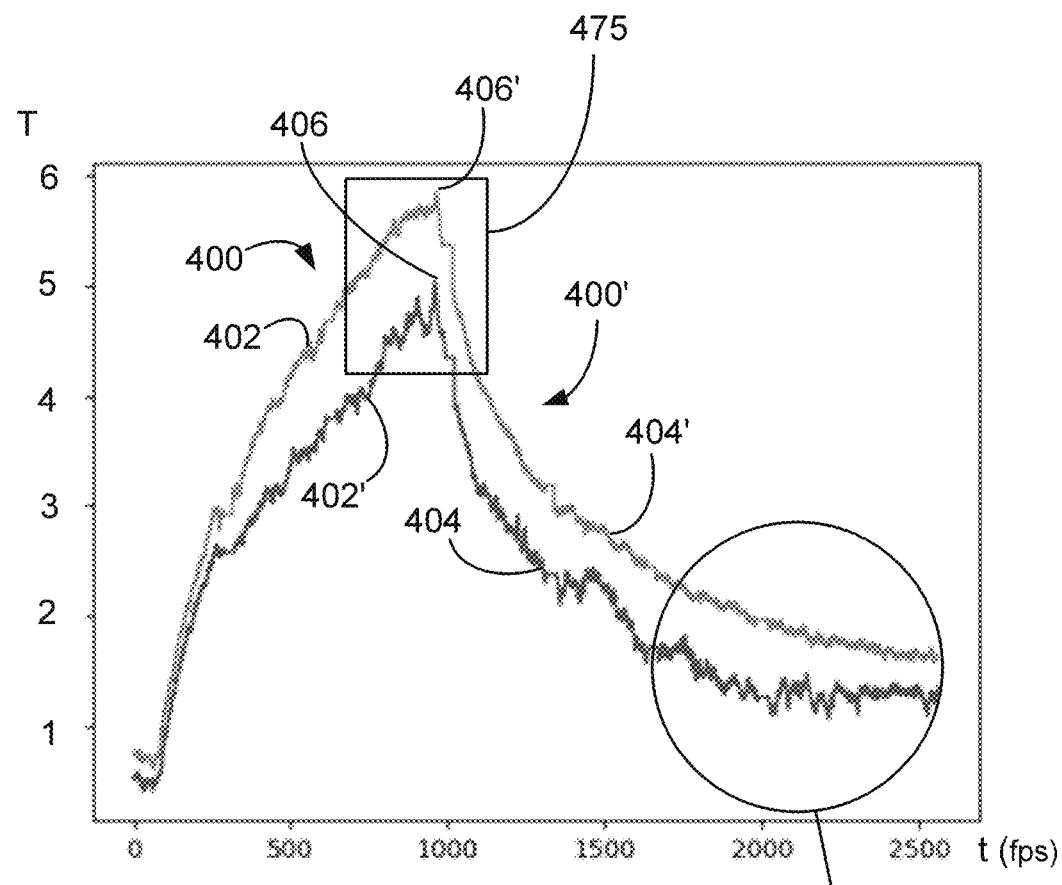
FIG. 4 is a graph of a thermal curve associated with biothermal behavior of tissue cells under temperature variation in accordance with some embodiments of the invention.
Figure 4:
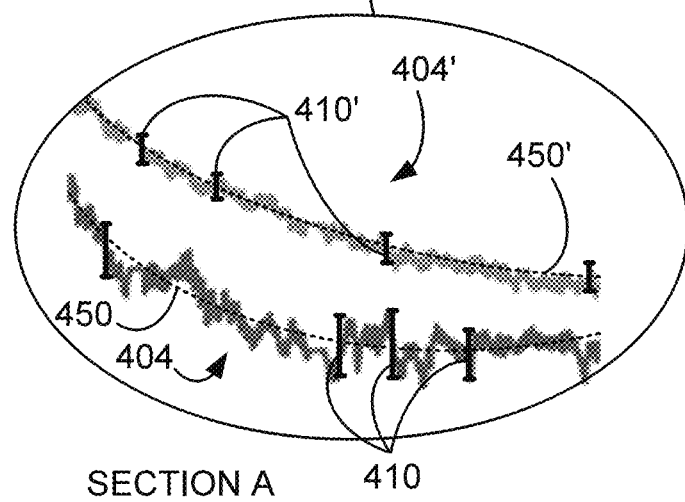

Reference is now made to FIG. 4, which is a graph of a thermal curve associated with biothermal behavior of heated tissue cells in accordance with some embodiments of the invention. FIG. 4 illustrates an exemplary embodiment of a pair of thermal behavior curves 400 and 400' over a period of time (t) obtained from two pixels P3 and P4 and compared by being drawn on the same T/t coordinate system. Variance between features representing portions of curves 400 and 400' can be defined not only along growing portions 402/402', decay portions 404/404' and/or of the locations of peak temperatures 406/406' as explained elsewhere herein, but also between features representing the seasonal noise along the portions.

As shown in an exemplary SECTION A of FIG. 4, there is a variance between respective curves 404 and 404' in the level of seasonal noise 410 and 410' measured in respect to an average median of the curves and expressed by phantom lines 450 and 450' respectively. In the exemplary embodiment shown in FIG. 4, the level of noise 410 of curve 400 in respect to an average median of a thermal behavior curve is greater than the level of noise 410' of curve 400'. It was found by the authors of this disclosure that various between features based on the level of noise in respect to an average median of a thermal behavior curve is specific to a tissue type or state and can therefore be used to indicate an existence of different tissue states or types in the imaged tissue.

Figure 5A:
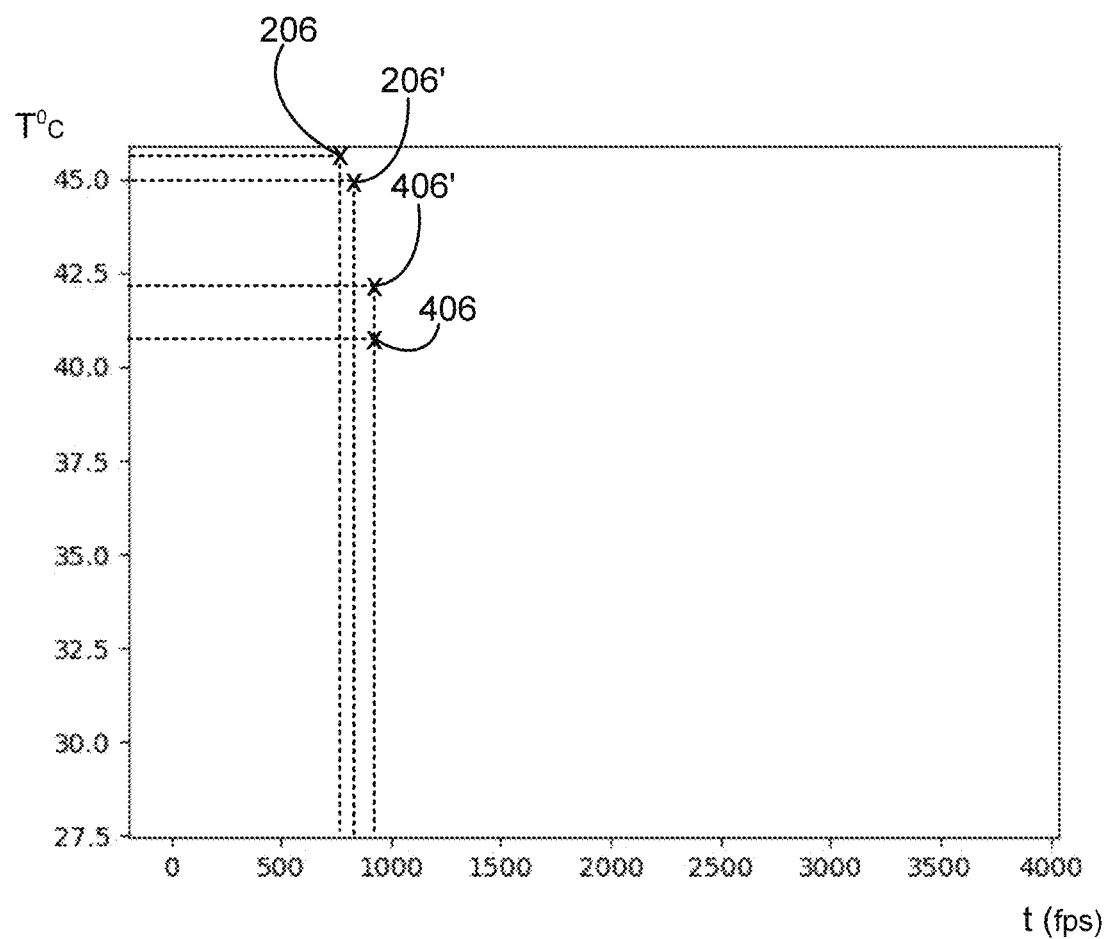
FIGS. 5A, 5B and 5C are graphs indicating peak temperature points in accordance with some embodiments of the invention.
Figure 5B:
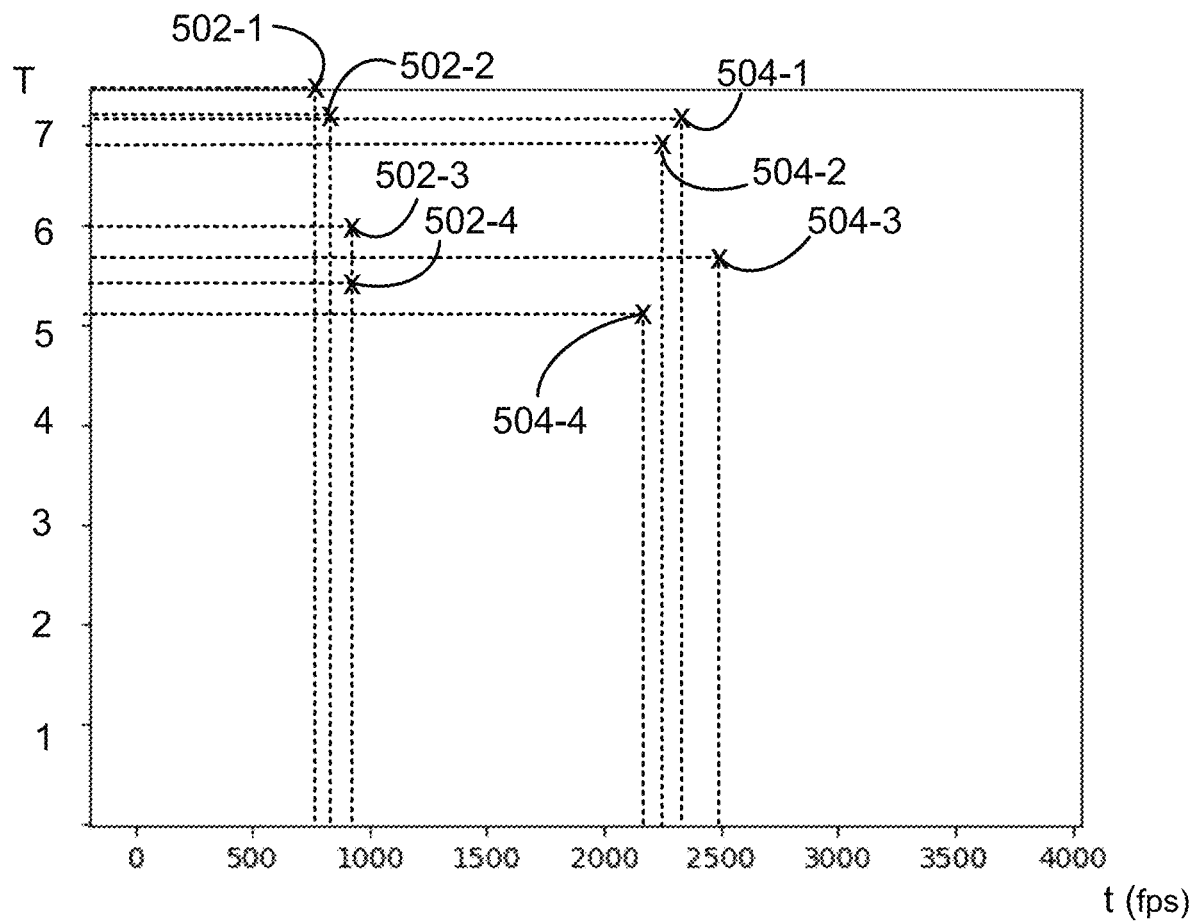
Figure 5C:
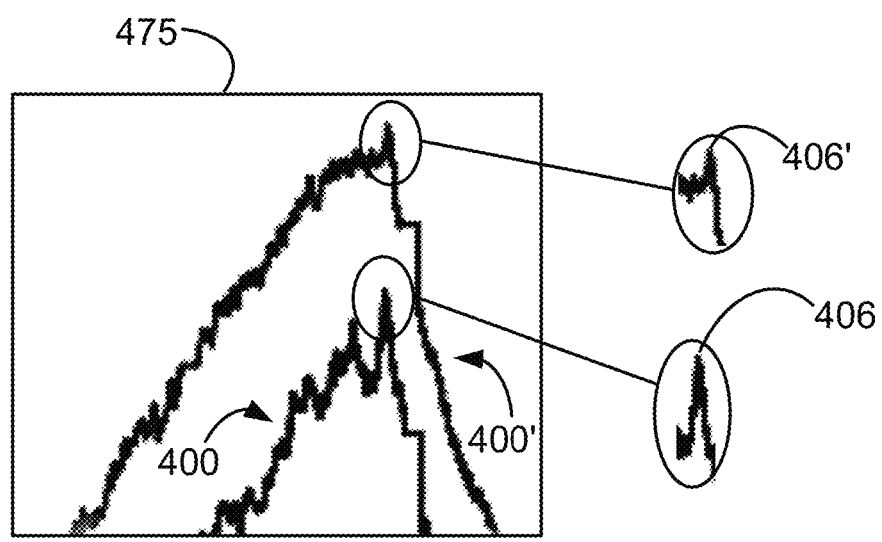

Reference is now made to FIGS. 5A, 5B and 5C, collectively referred to as FIG. 5, which is a graph analysis of peak temperature points 206/406 in accordance with some embodiments of the invention compared by being drawn on the same T/t coordinate system. Peak temperature points 206 and 206' are derived from thermal behavior curves 200/200' respectively and peak temperature points 406 and 406' are derived from thermal behavior curves 400/400' respectively as explained elsewhere herein. As depicted in the exemplary graph shown in FIG. 5, the variance between peak temperatures 206 and 206' is expressed in temperature and/or time of arrival at the peak temperature. However, the variance between peak temperatures 406 and 406' is expressed only in the temperature but peak temperatures 406 and 406' are shown to have arrived at the same time. Thermal imaging system 100 processor 110 is configured to identify variance in the coordinates of peak temperatures 206/206' and 406/406' and thereby be used to indicate an existence of different tissue states or types in the examined tissue.

In some embodiments and as depicted in FIG. 5C, which is portion 475 (Shown in FIG. 4) of an exemplary embodiment of a pair of thermal behavior curves 400 and 400' obtained from two pixels P3 and P4 and compared by being drawn on the same T/t coordinate system, a computer program product of processor 110 is configured to compare not just the variance between features based on peak temperatures 206 and 206' expressed in temperature and/or time of arrival at the peak temperature but also between features based on analysis of the shape of at least a portion of the graph leading to the peak (i.e., of the growing portion) and/or a portion of the graph following the peak (e.g., of the decaying portion).

As explained elsewhere herein, based on features representing the peak shape analysis, the computer program product of processor 110 is configured to identify on a generated output map a thermal signature specific to a tissue type or state imaged within an FOVp of a pixel, e.g., by identifying a thermal behavior pattern specific to a cell type.

In reference to FIGS. 3, 4 and 5, in some embodiments, thermal imaging system 100 processor 110 collects values from a plurality of pixels of imager 108 and groups the calculated results, e.g., features based on one or more of growth portions 202 in response to heating, a decay portions 204 during cooling, peak temperatures 206 at the meeting point of growth portion 202 and decay portion 204 and seasonal noise and define a cutoff lineation between groups displaying close or similar profiles. In some embodiments, and as shown in FIG. 5B, which is peak temperature points 206/406 compared by being drawn on the same T/t coordinate system, features based on peak temperature points 206/406 are grouped and identified by thermal imaging system 100 processor 110 as an early peaking group (502-1, 502-2, 502-3 and 502-4) that peaked e.g., under 1000 frames (e.g., at an imaging rate of 25 frames per second 1000 frames are imaged over four seconds) and identified as containing normal tissue based on a lookup table generated by thermal imaging system 100 processor 110 as explained elsewhere herein and a late peaking group (504-1, 504-2, 504-3 and 504-4) that peaked e.g., only over 2000 seconds and identified based on the lookup table as containing cancerous tissue.

As depicted in FIGS. 3, 4 and 5, in some embodiments, features representing peak temperature points such as peak temperature points 206/206'/506 and 506' can also be identified as thermal signatures of specific tissue states or types and clusters of similar peak temperature points identified by thermal imaging system 100 processor 110 can indicate clusters of tissue cells sharing the same tissue state in the examined tissue such as, for example, cancer tissue as explained in greater detail elsewhere herein.

In some embodiments and as disclosed elsewhere herein, the graph generated by thermal imaging system 100 processor 110 and shown. For example, in FIGS. 3 and 4 is based, among others on Pennes' bioheat equation wherein variables (a), (b), (c) and (d) can be at least any one of the following variables including environmental temperature, external heat source, tissue and/or organism metabolic heat source, heat loss due to blood perfusion, blood temperature, tissue density, specific heat, thermal conductivity factor, thermal conductivity coefficient, the thermal conductivity surface area (m2), the temperature of the object's surface and interior and the time-dependent thermal gradient between environment and object.

Tissue State and/or Type Characterization

In some embodiments, an array of pixels of imager 108 images a surface of tissue 104. In some embodiments, tissue 104 is preheated. Thermal imaging system 100 processor 110 receives and processes values from each pixel to create a map of the apparent temperature variance over the surface of the object. In some embodiments, each temperature value is assigned a different color. The resulting matrix of colors is sent to memory of thermal imaging system 100 processor 110 and to a system display as a thermal map (temperature distribution image) of surface of tissue 104.

Figure 6A:
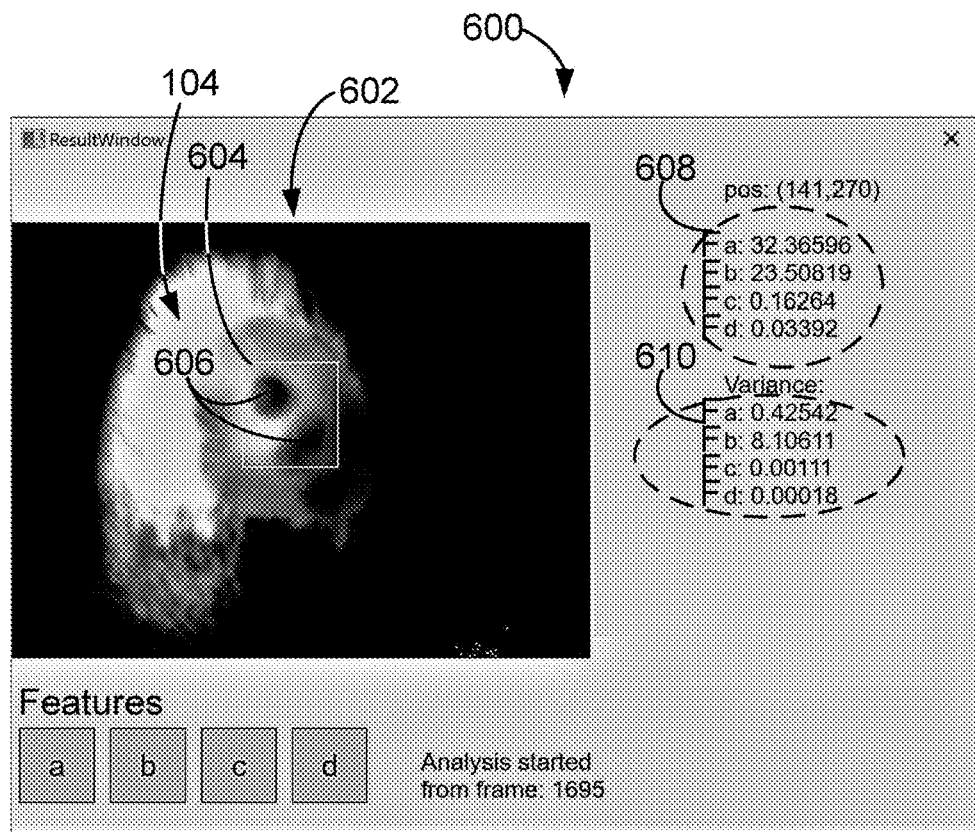
FIGS. 6A, 6B, 6C and 6D are exemplary screen image of a thermal imaging system display in accordance with some embodiments of the invention.
Figure 6C:
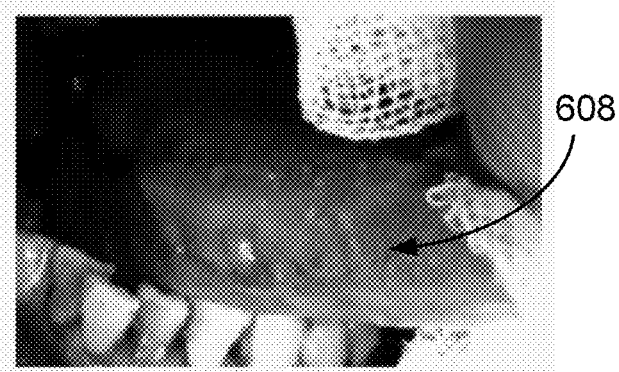
Figure 6D:
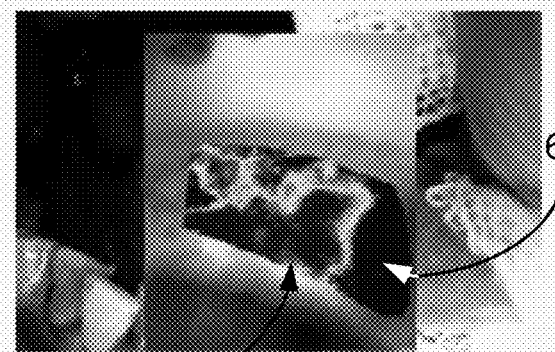
Figure 6B:
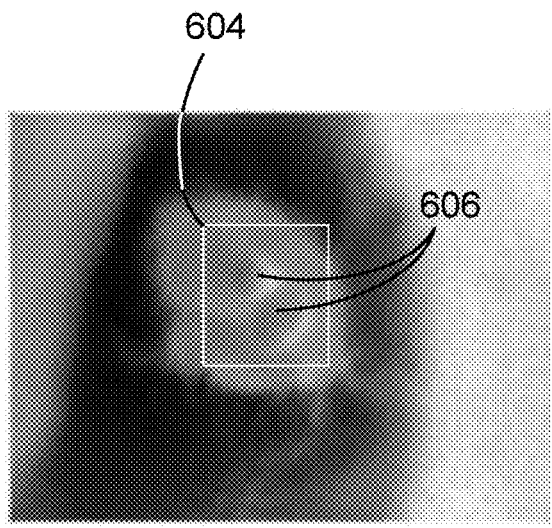

Reference is now made to FIGS. 6A, 6B, 6C and 6D, collectively referred to as FIG. 6, in which FIG. 6A is an exemplary thermal image 600 of a portion of mouse skin tissue 104 shown on system 100 display 112 in accordance with some embodiments of the invention. As shown in FIGS. 6A and 6B, thermal image 600 includes a thermal map 602. In some embodiments, an area of interest can be examined by moving a pixel group FOV indicator 604. In FIGS. 6A and 6B, for example, pixel group FOV indicator 604 is represented by a square white outline that represents the boundaries of a collective FOV of a group of pixels of the area of interest on surface of tissue 104. In some embodiments, indicator 604 is controlled, for example, by a joystick, computer mouse or similar control devices. In the exemplary embodiment shown in FIGS. 6A and 6B, pixel group FOV indicator 604 is placed over a segment of surface of tissue 104 and shows two aberrant tissue foci 606 e.g., suspected to be cancerous.

FIG. 6A illustrates an output map generated by a computer program product of processor 110 based on extracted feature sets (Fa), (Fb), (Fc), (Fd), clusters of the same feature sets or clusters of features from the same thermal image shown in FIG. 6A employing one or more other combinations of mathematical expressions used for the generated output map shown in FIG. 6A. In FIG. 6A, two aberrant tissue foci 606 e.g., suspected to be cancerous are identified by computer program product of processor 110. In comparison, FIG. 6B, which is a white-light image of the same FOV imaged in FIG. 6A. In the image of 6B, areas 606 identified in the generated output map shown in FIG. 6A appear to be the same as the tissue surrounding them. As shown in FIG. 6C, the gum tissue 608 appears in an RGB photograph as generally uniform, even-colored gum tissue. In contrast, the thermal diffusion map of FIG. 6D demarcates a large segment 610 of abnormal gum tissue in respect to the surrounding normal tissue 612. In this specific example, the abnormal gum tissue is identified as cancerous tissue.

In some embodiments and as shown in FIGS. 6C and 6D, which are an RGB photograph of human gums (FIG. 6C) and a processed and generated thermal diffusion map (FIG. 6D) super imposed over an RGB photograph of the tissue.

In some embodiments, a method for differentiating between tissue states or types includes actively changing a temperature a surface of at least a portion of tissue from a base temperature (Tb) over a predetermined first period of time (t0 to t1), followed by stopping effecting the temperature change and allowing temperature of the tissue to passively return to the base temperature over a second period of time (t1 to t2), while obtaining during said first and second periods of time (t0 to t2) a plurality of thermal images of the imaged surface of said tissue.

In some embodiments, the method includes processing thermal values received from the imager 108 pixels to generate one or more values that are associated with one or more physiological or pathological parameters of the tissue, comparing the values with a database e.g., lookup table of signature data associated with one or more tissue states or types and generating an output indicating on the obtained image identification of tissue states or types of tissue cells and/or demarcation of boundaries of the identified regions of tissue cells being in the same tissue state.

In some embodiments, indicating and/or identifying tissue states or types includes one or more of tracking changes over time in thermal values received from imager pixels, identifying patterns in said changes and classifying or grouping the patterns of changes into classifications or groups. This is followed by comparing the classified patterns with signature patterns of tissue states or types, associating each classification with a database of predetermined signature patterns of tissue states or types and identifying tissue states or types and/or associating areas within the obtained thermal images containing tissue in the identified tissue states or types.

Figure 7:
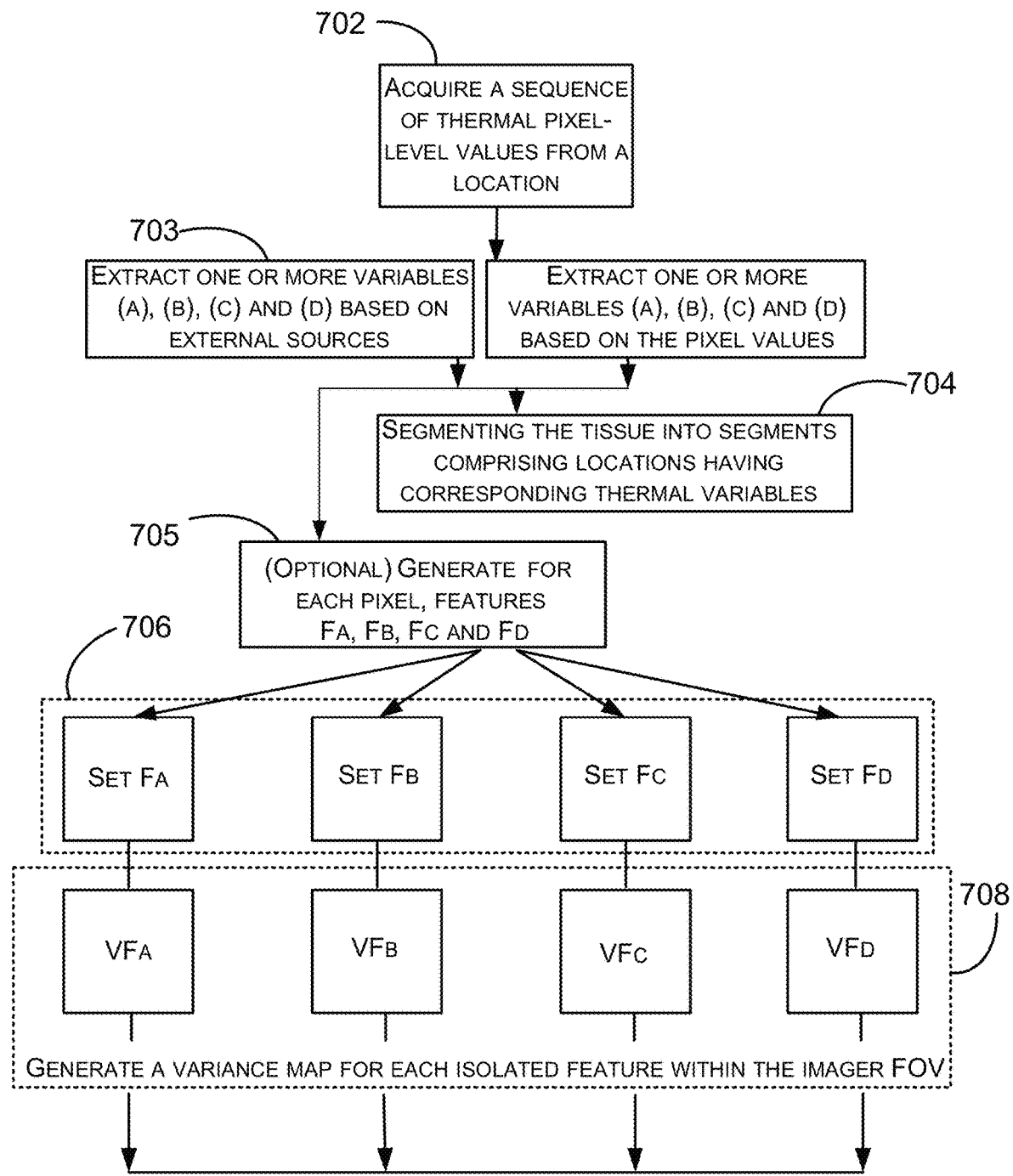
FIG. 7, which is an exemplary simplified flow chart illustrating operation of thermal imaging system processor in accordance with some embodiments of the invention.
Figure 7:
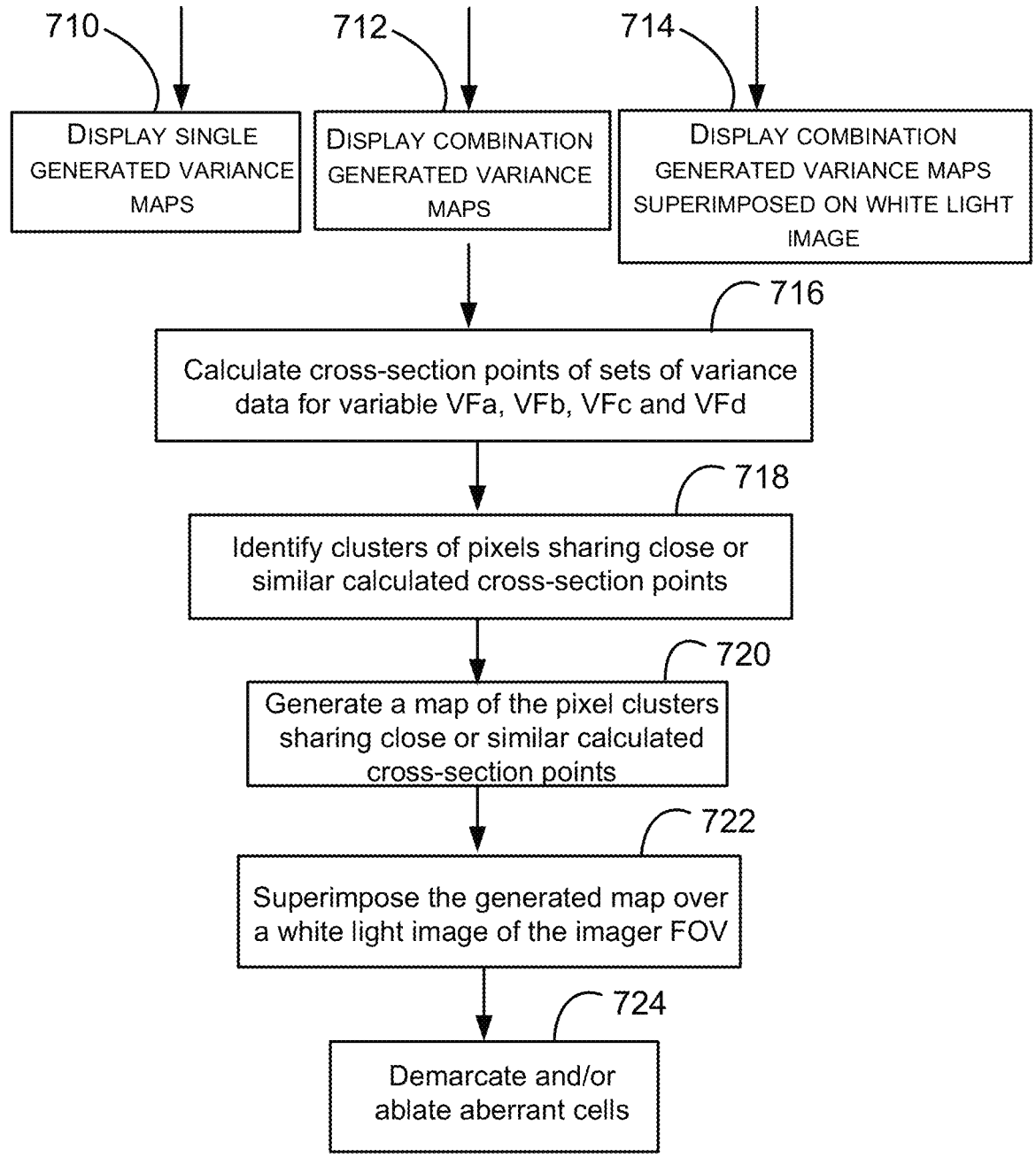

The following is one example of the above described method for differentiating between tissue states or types. Reference is now made to FIG. 7, which is an exemplary simplified flow chart illustrating operation of thermal imaging system 100 processor 110 in accordance with some embodiments of the invention. As shown in FIG. 7, at 702 thermal imaging system 100 processor 110 is configured to acquire from imager 108 a sequence of thermal images of surface of tissue 104 over a period of time.

In some embodiments and as explained elsewhere herein, thermal imaging system 100 processor 110 is configured to extract at 703 one or more variables (a), (b), (c) and (d) derived from Pennes' biothermal conductivity equation and/or derive one or more variables (a), (b), (c) and (d) from at least any one of external parameters affecting thermal behavior of the cell e.g., environmental temperature, external heat source and interior and the time-dependent thermal gradient between environment and object and/or intrinsic tissue parameters affecting thermal behavior of the cell (thermal parameters) e.g., tissue and/or organism metabolic heat source, heat loss due to blood perfusion, blood temperature, tissue density, specific heat, thermal conductivity factor, thermal conductivity coefficient, the thermal conductivity surface area (m2) and the temperature of the object's surface.

In some embodiments, thermal imaging system 100 processor 110 is configured at 704 to segment the tissue into segments comprising locations having corresponding one or more thermal variable and, optionally, generate an output indicating the tissue segments.

Optionally, at 705, thermal imaging system 100 processor 110 is configured to calculate for each pixel one or more features e.g., (Fa), (Fb), (Fc) and (Fd) based on the one or more extracted variables (a), (b), (c) and/or (d). In some embodiments, and as explained elsewhere herein, calculated features (Fa), (Fb), (Fc) and (Fd) represent thermal behavior of the imaged tissue cells affected, at least in part by thermal parameters as listed elsewhere herein. In some embodiments and as showed in FIG. 6, thermal imaging system 100 processor 110 displays on display 600 calculated features of at least features (Fa), (Fb), (Fc) and (Fd) e.g., in a form of a list 608 or a map depicting distribution of calculated features (Fa), (Fb), (Fc) and (Fd) in the imaged area.

At 706 thermal imaging system 100 processor 110 compiles from each pixel within the FOV of imager 108 one or more sets of the features calculated at step 705 and processes for each set of one or more features (Fa), (Fb), (Fc) and (Fd), and generates at 708 a variance map for each of the sets or groups compiled at 706 (VFa, VFb, VFc and VFd).

As explained elsewhere herein, calculated features (Fa), (Fb), (Fc), (Fd) and other contributing features, groups of the same features or groups of features from one or more thermal images are processed by a computer program product of processor 110, using data mining processes, e.g., to cross-reference data, perform data cleansing, and generate an output in a form of a map indicating and/or identifying various tissue states or types within the imaged tissue area.

In in the exemplary embodiment, depicted in FIG. 6, thermal imaging system 100 processor 110 displays on display 600 an output map generated by a computer program product of processor 110 showing calculated variance of values of at least features (Fa), (Fb), (Fc) and (Fd) as a list 610.

In some embodiments and optionally and as shown in FIG. 7, at 710, variance maps for each of the compiled sets at 706 (VFa, VFb, VFc and VFd) of the at least features (Fa), (Fb), (Fc) and (Fd) over the FOV of imager 108 are displayed on e.g., display 600 in sequence at 710, or in any combination (e.g., one or more super imposed on each other) at 712, or in any combination and super imposed over a RGB image of imager 108 FOV at 714 to identify aberrant tissue (e.g., cancerous tissue) in accordance with a lookup table based on a predetermined gold standard benchmark, which increases accuracy of the thermal image analysis process.

In some embodiments and optionally, thermal imaging system 100 processor 110 calculates at 716 cross-section points of one or more data sets e.g., variance between feature sets (VFa, VFb, VFc and VFd) generated at 708 and identifies at 718 one or more groups of pixels having close or similar calculated cross-section points. At 720, thermal imaging system 100 processor 110 generates a map corresponding to location of identified pixel groups from which analysis of values obtained results in cross-section points closest to values, variables and/or features defined by a predetermined gold standard benchmark and at 722 and at 724, thermal imaging system 100 processor 110 superimposes the map generated at 720 over a RGB image of imager 108 FOV to assist the health professional identify the location of suspicious cell clusters on the surface of tissue 104.

In some embodiments, cross-section points of one or more data sets e.g., variance data sets (VFa, VFb, VFc and VFd) identified by thermal imaging system 100 processor 110 correspond to areas of congruence in overlapping maps of variance data sets (VFa, VFb, VFc and VFd). In some embodiments and as explained elsewhere herein, system 100 comprises a source of illumination 114 that illuminates the tissue and demarcates surgical borders for removal of aberrant tissue. Alternatively, or additionally and optionally, in some embodiments system 100 comprises a source of ablative energy 116 to ablate the demarcated aberrant tissue. In some embodiments and optionally at 724, thermal imaging system 100 processor 110 identifies the location of suspicious cell clusters on the surface of tissue 104 and provides outline coordinates of the suspicious cell clusters to source of illumination 114 that demarcates surgical borders for removal of aberrant tissue and/or to source of ablative energy 116 that applies ablative energy 116 to ablate the demarcated aberrant tissue.

Returning to the exemplary embodiment depicted in FIG. 6, screen image 600 of system 100 display 112 displays a pixel group FOV at a specific set of coordinates (pos: 141, 270) displayed within square white outline 604. In some embodiments, frame 604 is positioned at (pos: 141, 270) to identify suspected aberrant tissue masses 608 e.g., as cancerous or non-cancerous.

In some embodiments, the method includes a quick superficial thermal scan over a large area and identifying suspicious foci followed by close and meticulous imaging of the suspected foci or regions of cells by bringing at least a portion of the region within square white outline 604.

In some embodiments, screen image pixel clusters 606/608 represent pixel clusters (and therefore imaged tissue cell clusters) sharing one or more features comprising a variance in respect to surrounding pixels (and therefore imaged tissue) calculated by thermal imaging system 100 processor 110 based on one or more variables (a), (b), (c) and (d) as explained elsewhere herein.

In some embodiments, and as explained elsewhere herein, the generated variance map for each isolated value of predetermined features (Fa), (Fb), (Fc) and (Fd) within the imager FOV or any combination thereof is superimposed over a RGB image of the imaged tissue to make suspected cell clusters identifiable to a naked eye.

In some embodiments, the present disclosure may provide for implementing machine learning algorithms and/or techniques, e.g., for determining a tissue state. In some embodiments, at a training stage, an exemplary machine learning classifier of the present disclosure may be configured to receive, obtain, and/or otherwise having received or obtained a dataset comprising a plurality of tissue thermal parameters, features, and/or variables relating to a plurality of subjects. In some embodiments, these thermal parameters, features, and/or variables are the same or substantially similar to those fully described in detail elsewhere herein.

In some embodiments, a preprocessing stage may include data preparation. Data preparation may include cleaning data, transforming data, and/or selecting subsets of records. In some embodiments, data preparation can include executing pre-processing operations on the data. For example, an imputation algorithm can be executed to generate values for missing data. Up-sampling and/or predictor rank transformation can be executed (e.g., for variable selection) to accommodate class imbalance and non-normality in the data. In some embodiments, executing the imputation algorithm includes interpolating or estimating values for the missing data, such as by generating a distribution of available data for a clinical parameter having missing data, and interpolating values for the missing data based on the distribution.

In some embodiments, a time handling step may be configured to generate a time-dependent representation of one or more parameters, features, and/or variables using, for example, a Fourier transform, polynomial adjustments, decay equations, and/or various statistical tools. In some embodiments, the time handling step may include automatically and/or manually combining a plurality of measurements taken from a subject over a sequence of time periods to determine and/or create a at least one combined parameter and/or feature which may represent patterns of change of the plurality of measurements over time and/or time-series variables.

In some embodiments, a feature extraction step may be configured to generate additional features, e.g., based on relations between existing features in the dataset, and add the additional features to the dataset.

In some embodiments, variable selection may be performed to, e.g., identify the most relevant variables and predictors from the set of obtained parameters. In some embodiments, variable and/or variable selection can include executing supervised machine learning algorithms, such as constraint-based algorithms, constraint-based structure learning algorithms, and/or constraint-based local discovery learning algorithms. In some embodiments, variable selection can be executed to identify a subset of variables in the training data which have desired predictive ability relative to a remainder of the variables in the training data, enabling more efficient and accurate predictions using a model generated based on the selected variables. In some embodiments, variable selection is performed using machine learning algorithms, e.g., Analysis of variance (ANOVA), a boosting ensemble such as XGBoost, Grow-Shrink ("gs"), Incremental Association Markov Blanket ("iamb"), Fast Incremental Association ("fast, iamb"), Max-Min Parents & Children ("mmpc"), or Semi-Interleaved Hiton-PC ("si.hiton.pc") algorithms. However, various other implementations of such machine learning algorithms may be used to perform variable selection and other processes described herein. In some embodiments, variable selection can search for a smaller dimension set of variables that seek to represent the underlying distribution of the full set of variables, which attempts to increase generalizability to other data sets from the same distribution.

In some embodiments, variable selection may be performed by removing variables that are highly correlated. Several algorithms can be used to search the input dataset with ranked predictors to find a reduced variable set that best represented the underlying distribution of all variables with respect to the infectious complication outcomes. A variable selection filter algorithm can be used to choose the reduced variable set. For example, in some embodiments, one or more of the Maximum Minimum Parents Children (mmpc) and/or the inter-iamb algorithm can be used to choose the nodes of the corresponding Bayesian network as the reduced variable set.

In some embodiments, variable selection is performed to search the training data for a subset of variables which are used as nodes of Bayesian networks. A Bayesian network (e.g., belief network, Bayesian belief network) is a probabilistic model representing a set of variables and their conditional dependencies using a directed acyclic graph. For example, in the context of diagnostic prediction, variable selection can be used to select variables from the training data to be used as nodes of the Bayesian network; given values for the nodes for a specific subject, a prediction of a diagnosis for the subject can then be generated.

In some embodiments, a training dataset for a machine learning classification model of the present disclosure is created, based, at least in part, on the collected parameters and the variable selection process performed as described above. In some embodiments, the training dataset comprises parameters, features, and/or variable sets associated with various tissue states or types in subjects. The values of the parameters can be received and stored for each of a plurality of subjects. The training dataset can associate the values of the plurality of parameters, features, and/or variable to the corresponding tissue state for each of the plurality of subjects. In some embodiments, the parameters, features, and/or variable sets may be labelled with the corresponding tissue state.

In some embodiments, a machine learning classifier of the present disclosure is trained on the training dataset to generate a classification model. For example, the machine learning classifier can execute classification algorithms (e.g., binary classification algorithms) for each subset of model parameters to generate predictions of tissue state. In some embodiments, the classification algorithms including but not limited to linear discriminant analysis (IDA), classification and regression trees (CART), It-nearest neighbors (KNN), support vector machine (SVM), Gaussian support vector machine (GSVM), logistic regression (GLM), random forest (RF), generalized linear models (GLMNET), and/or naive Bayes (NB). In some embodiments, classification may be defined as the task of generalizing a known structure to be applied to new data. Classification algorithms can include linear discriminant analysis, classification and regression trees/decision tree learning/random forest modeling, nearest neighbor, support vector machine, logistic regression, generalized linear models, Naive Bayesian classification, and neural networks, among others. In some embodiments, a trained machine learning classification model of the present disclosure can include, e.g., cluster analysis, regression (e.g., linear and non-linear), classification, decision analysis, and/or time series analysis, among others. In some embodiments, where variable selection is performed prior to generated the random forest model, the training data is sampled based on the reduced set of variables from variable selection (as opposed to sampling based on all variables).

In some embodiments, after the training stage, a trained machine learning classifier of the present disclosure may be configured to implement a validation process, e.g., through a first evaluation which may include, e.g., a cross-validation. The cross validation may be configured to randomly divide the training set into, e.g., ten folds. The ten-fold validation may then run ten times, for example, using nine different folds of the training set for machine learning modeling, and a tenth fold for validation. The results may be assessed through a computation of statistical measures, e.g., average and a confidence interval of an Area Under a Receiver Operating Characteristic curve (AUROC) for the ten different evaluation folds. In some embodiments, a second evaluation may include an assessment of a machine learning model on a validation set, e.g., the tenth fold for validation which may include 10% of the original data. In some embodiments, a third evaluation may include a statistical analysis, for example, including presenting population characteristics by median and InterQuartile Range (IQR) for skewed data, and a mean with standard deviation for normal distributed data, e.g., using bootstrapping techniques. In some embodiments, a cross validation process of the machine learning model may implement a statistical method configured to estimate a skill of a machine learning model on a limited data sample, e.g., in order to estimate how the machine learning model is expected to perform when used to make predictions on data which was not used when training the machine learning model. In some embodiments, the cross validation process of the machine learning model may include splitting a given data sample into a plurality of groups and/or folds, for example, ten groups and/or folds.

In some embodiments, a trained machine learning classifier fop the present disclosure can be applied, at an inference stage, to a received thermal video stream of a tissue, the generate one or more predictions as to a state of regions within the tissue.

In some embodiments, unsupervised classification models may be employed, using, e.g., to extract parameters, features, and/or variables in an unsupervised manner from thermal image streams of a tissue. In some embodiments, such extracted parameters, features, and/or variables may then be used as an input to the trained machine learning classifier described above.

Figure 8A:
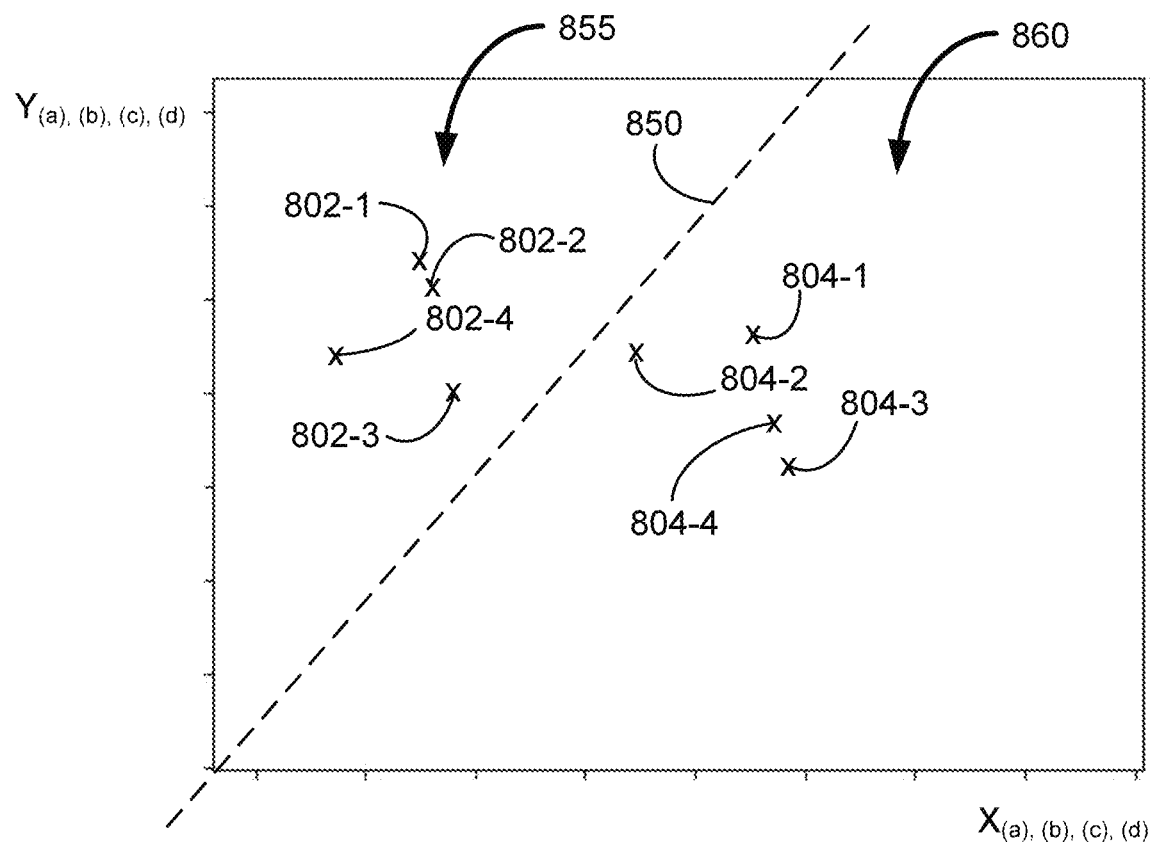
FIGS. 8A and 8B are simplified graphs illustrating variance data sets of cross-section points in accordance with some embodiments of the invention.
Figure 8B:
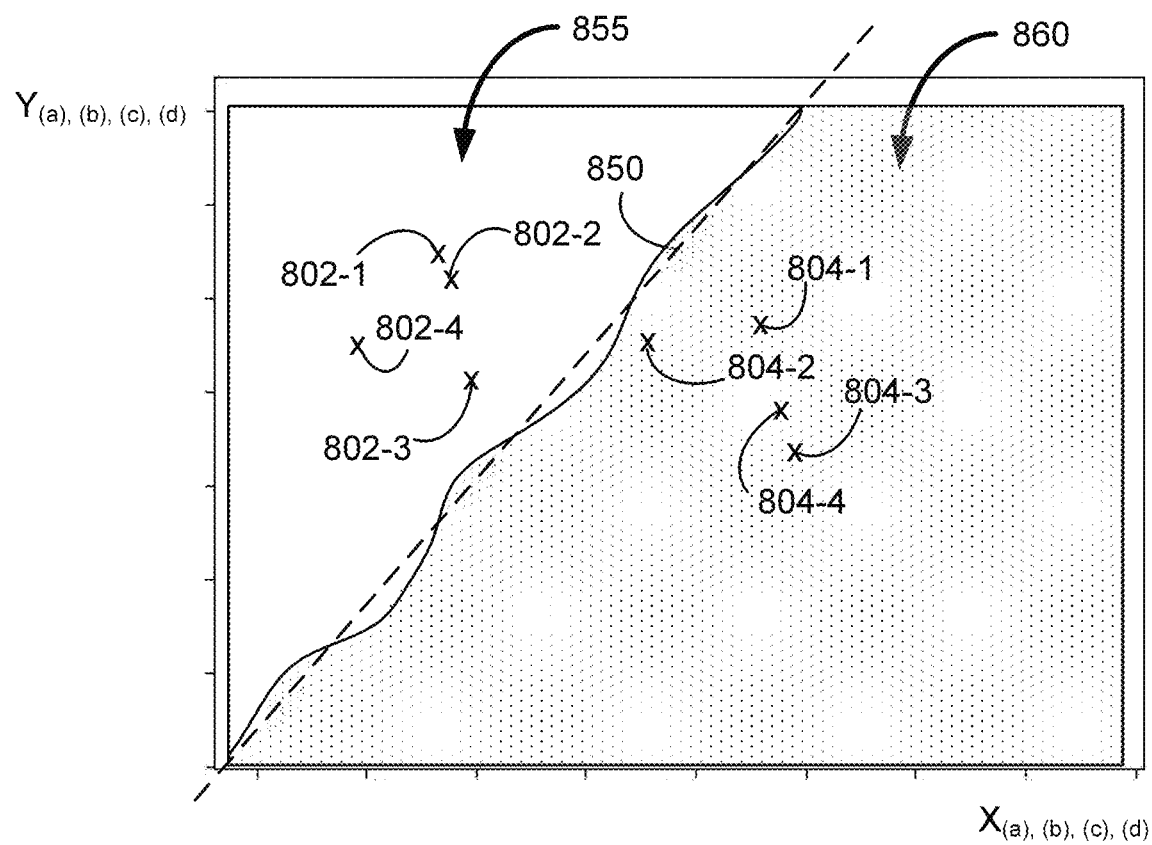

Reference is now made to FIGS. 8A and 8B, which are simplified graphs illustrating variance data sets or groups of cross-section points in accordance with some embodiments of the invention. In some embodiments, processor 110 is configured to select and process variance in sets of pixel-level values or of thermal variables or features based on the pixel-level values such as the sets depicted in FIGS. 8A and 8B that are closest to values of pixel-level values, thermal variables or features defined by a predetermined gold standard benchmark. As shown in the exemplary graph shown in FIG. 8, cross-section points 802 and 804 are clustered into one or more clusters (e.g., 802-1, 802-2, 802-3 and 802-4 and/or 804-1, 804-2, 804-3 and 804-4).

As explained elsewhere herein, thermal imaging system 100 processor 100 is configured to identify associate pixels with generated cross-section points 802 and 804 and delineate a border 850 between a first type of tissue associated with cross-section points 802 in a section 855 on surface of tissue 104 and a second type of tissue associated with cross-section points 804 in a section 860 on surface of tissue 104. The states or types of tissue 802 and 804 identified histologically are registered in a lookup table stored in a memory of thermal imaging system 100 processor 110 for future reference.

Alternatively and optionally, in some embodiments, thermal imaging system 100 processor 100 is configured to compare clusters 802/804 against a pre-compiled lookup table, identify tissue states or types 802 as a first type of tissue (e.g., healthy tissue) in tissue section 855 and tissue states or types 804 as a second type of tissue (e.g., cancerous tissue) in tissue section 860 and delineate a border 850 between tissue sections 855 and 860. Additionally and optionally, in some embodiments, thermal imaging system 100 processor 110 is configured to map the identified tissue states or types 802 and 804 and display the map on display 112 superimposed on a RGB image of imager 108 FOV as shown in FIG. 8B.

Heat Application Techniques
Vector Heating

The term "Vector" heating as used herein relates to heating along a path that may follow any pattern and not necessarily along a straight line.

Figure 9A:
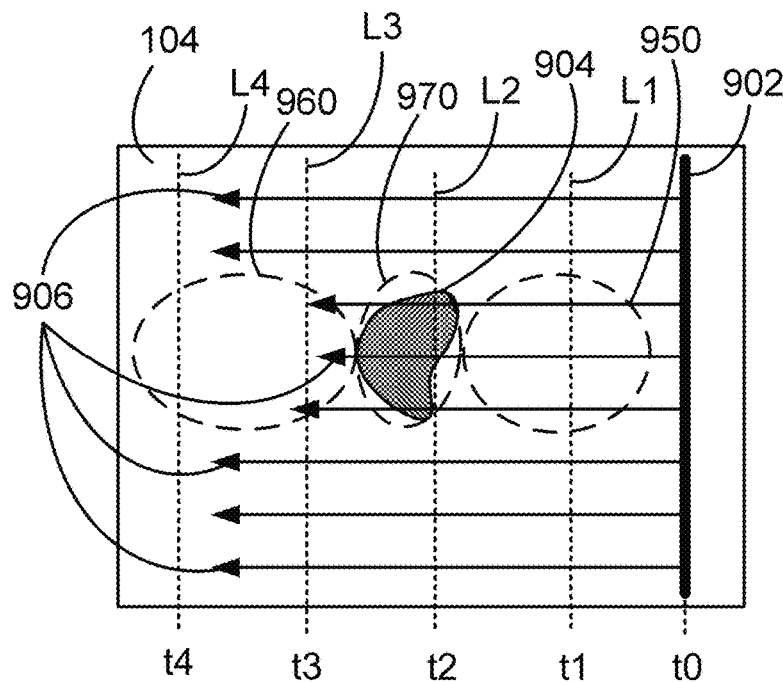
FIG. 9A is a planar view simplified illustration of heat distribution over a portion of a surface of tissue in accordance with some embodiments of the invention.
Figure 9B:
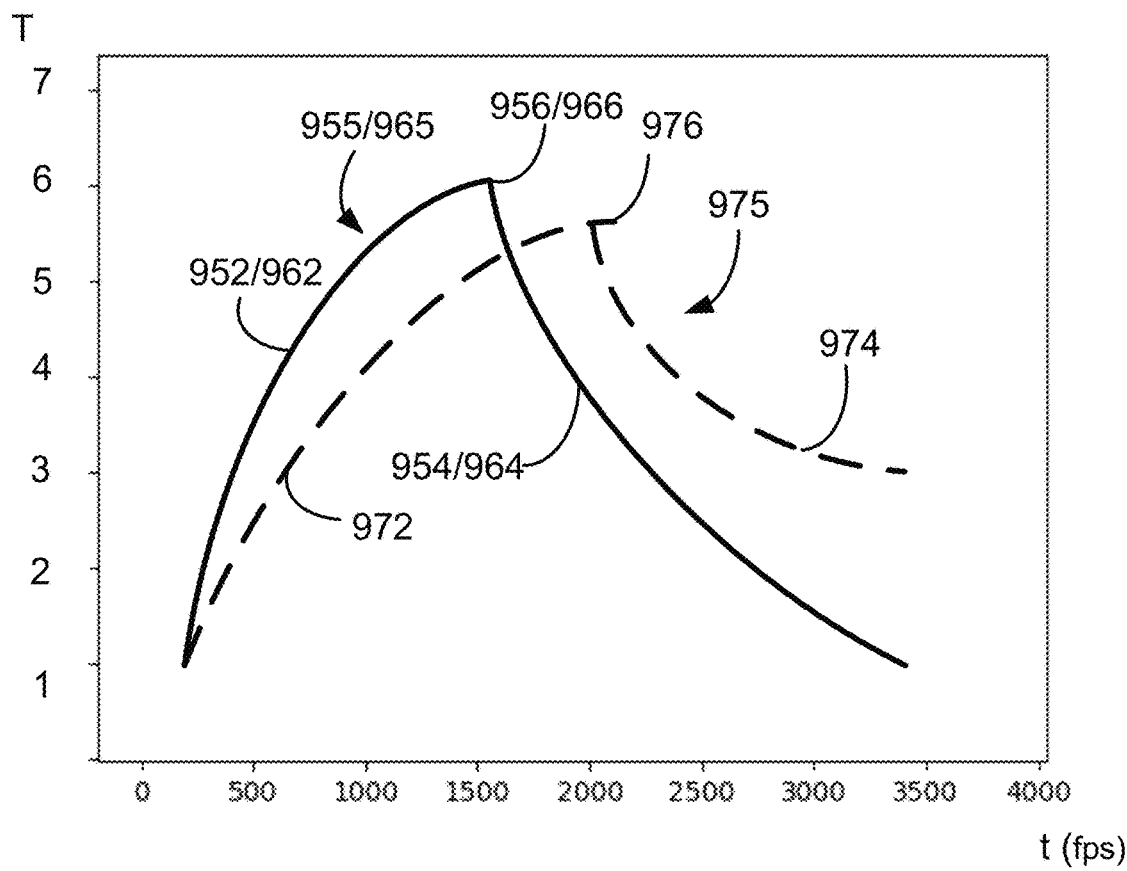
FIG. 9B is a thermal graph of cells within the portion of the surface of tissue in accordance with some embodiments of the invention.

Reference is now made to FIGS. 9A, which is a planar view simplified illustration of heat distribution over a portion of a surface—in accordance with some embodiments of the invention and 9B, which is a thermal graph of tissue within the portion of the surface of tissue in accordance with some embodiments of the invention.

As shown in the exemplary embodiment depicted in FIG. 9A a surface of tissue is heated along a line 902 disposed to one side of a suspected aberrant tissue 904. For clarity of explanation, heat distribution from line 902 in a direction away from the suspected aberrant tissue is ignored.

In some embodiments, thermal imaging system 100 is configured to obtain a plurality of thermal images of an FOV of imager 108 over a set period of time (t) and process consecutive frames of the plurality of images to extract information regarding variances in thermal parameters of tissue cells over the set period of time.

In some embodiments, thermal imaging system 100 compares speed of heat diffusion through the tissue cells within the FOV of imager 108 in a direction indicated by arrows 906 over one or more periods of time (e.g., t1, t2, t3, t4) measured from a heat application time (t0). In some embodiments, temperature measurements at periods of time (t1), (t2), (t3) and (t4) are taken along lines (e.g., L1, L2, L3 and L4) parallel to heating line 902.

As shown in the embodiment depicted in FIG. 9A, during a period of time (t3) the distribution of heat generated by line 902 is uniform over most of the surface of tissue 104 within the FOV of imager 108. However, measurements within an area 970 delineated by a broken-line circle show a slower diffusion of heat through tissue cells within that area as compared to the majority of the area of surface of tissue 104 including delineated areas 950 and 960 on either side of area 970. Thermal imaging system 100 processor 110 is configured to identify the variance in speed of diffusion through the tissue cells inside area 970 to be associated with a variance in one or more physiological or pathological/thermal parameters associated with the tissue within area 907 and surrounding tissue and marks area 970 as containing tissue suspicious to be aberrant (e.g., cancerous).

Additionally, and optionally, in some embodiments and as explained in greater detail elsewhere herein, thermal imaging system 100 processor 110 is configured to process thermal graphs of tissue within the FOV of imager 108. As shown in the exemplary embodiment depicted in FIG. 9B, which is a graph of a thermal curve associated with biothermal behavior of heated tissue in accordance with some embodiments of the invention, curve 955/965 represents thermal curves of tissue surrounding suspected tissue within area 970, for example, tissue in area 950 and/or 960, wherein curve 975 represents the thermal curve obtained from tissue within area 970.

The graphs displayed by thermal imaging system 100 processor 110 show that the overall thermal behavior of tissue cells i.e., response to heating within area 970 is slower than thermal behavior of tissue cells i.e., response to heating within areas surrounding area 970 e.g., areas 950/960. This is indicated for example, by a shallow growth portion 972 of curve 975 in response to heating in respect to a steeper growth portion 952/962 of curve 955/965. Additionally, and optionally, curve 975 arrives at peak temperature 976 later than curve 955/96, which indicates slower thermal behavior of tissue within area 970. Decay portion 974 exhibits slower thermal behavior of the tissue within area 970 indicated by a shallow curve in respect to decay portion 954/964 of curve 955/965 similarly to shallow growth portion 972.

In some embodiments and as explained in greater detail elsewhere herein, thermal imaging system thermal imaging system 100 processor 110 is configured to process the variances exhibited all along thermal behavior curves 975 and 955/965 by processing and compares the graphs as a whole or processing only portions of the curves such as only growing portions 972 and 952/962, only decay portions 974 and 954/964, only by peak temperatures 976 and 956/966 location or any combination thereof and generates a thermal signature derived from the variance between the thermal behavior curves 975 and 955/965 exhibited by the shape of the thermal behavior curve leading to a peak temperature and decaying therefrom and identifies specific tissue states or types associated with the thermal signature. In some embodiments, thermal imaging system 100 processor 110 processes information received from at least a portion of an array of pixels as explained in greater detail herein and use the information to indicate an existence of different tissue states or types in the examined tissue (e.g., normal tissue versus cancerous tissue).

In some embodiments, accuracy and specificity of the tissue type or state identification can be increased by heating surface of tissue 104 along one or more lines 902 disposed to one side of a suspected aberrant tissue 904. In the exemplary embodiments depicted in FIGS. 10A, 10B and 10C, which are planar view simplified illustrations of heat distribution over a portion of a surface of tissue in accordance with some embodiments of the invention surface of tissue 104 is heated along lines 902/1002 disposed to one side of a suspected aberrant tissue 904. In some embodiments, lines 902 (FIG. 10A) and 1002 (FIG. 10B) are perpendicular to each other.

Figure 10A:
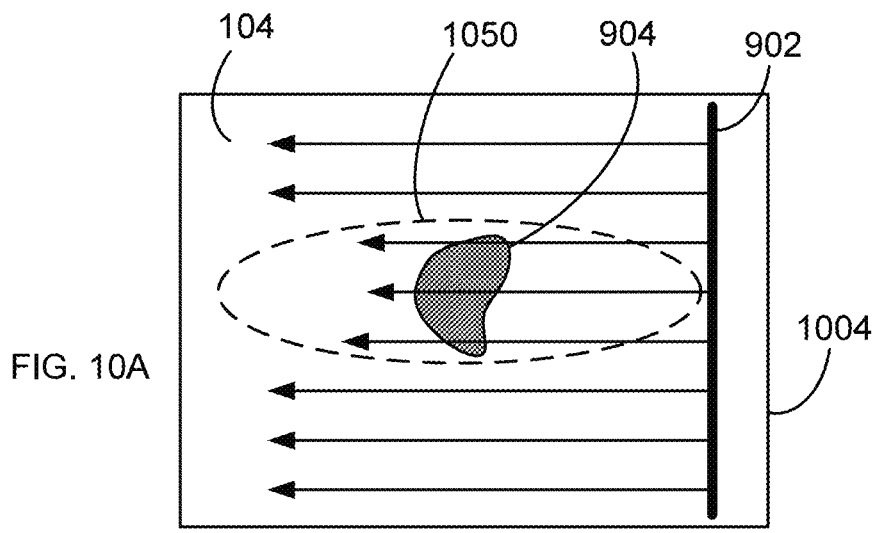
FIGS. 10A, 10B and 10C are planar view simplified illustrations of heat distribution over a portion of a surface of tissue in accordance with some embodiments of the invention.
Figure 10B:
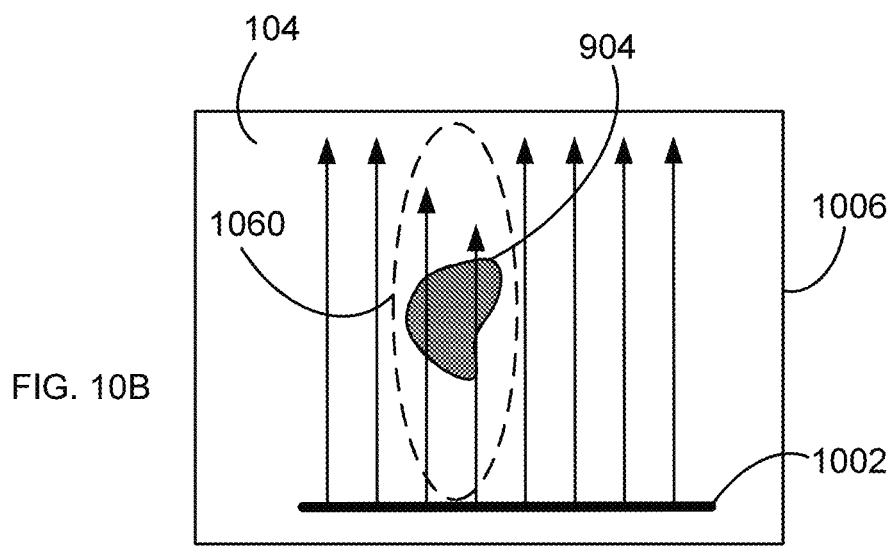
Figure 10C:
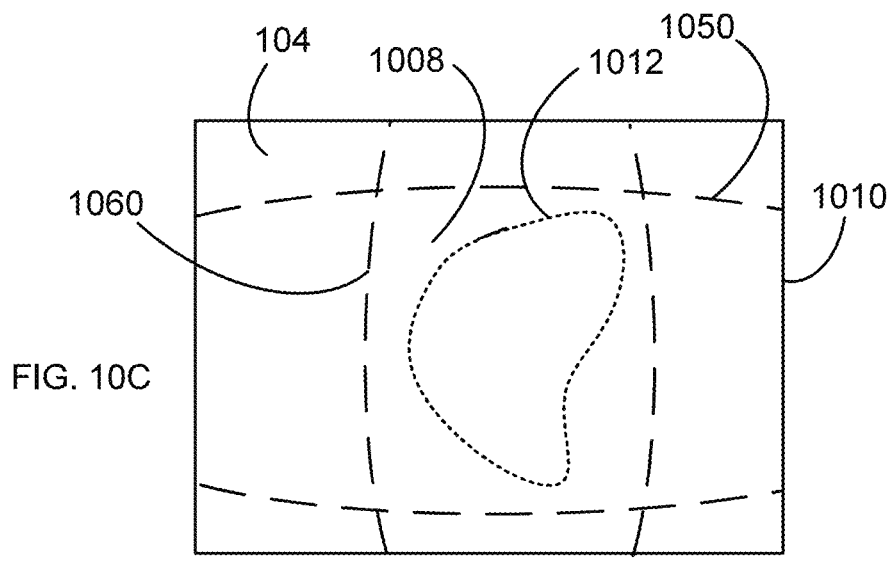

As shown in FIG. 10C, thermal imaging system 100 processor 110 is configured to compile the thermal behavior data obtained from thermal images 1004 and 1006 shown in corresponding FIGS. 10A and 10B, extract information regarding one or more physiological or pathological thermal parameters associated with cells identified as aberrant tissue cells in both thermal images 1004 and 1006, mainly within an area 1008 and generate at least an outline of suspected aberrant tissue 904.

In some embodiments, the duplicity of at least part of the values obtained by thermal imaging system 100 processor 110 and comparison between obtained values from image 1004 and values obtained from image 1006 increases accuracy and specificity of the tissue type or state identification and location. This enables thermal imaging system 100 processor 110 to enlarge (i.e., zoom-in) area 1008 shown in FIG. 10C and more accurately delineate the outline 1012 of suspected aberrant tissue 904. In some embodiments, thermal imaging system 100 processor 110 is configured superimpose the outline of suspected aberrant tissue 904 onto a RGB image of surface of tissue 104 to assist the health professional clearly and accurately identify the borders of suspicious cell cluster 904 on the surface of tissue 104.

Figure 11A:
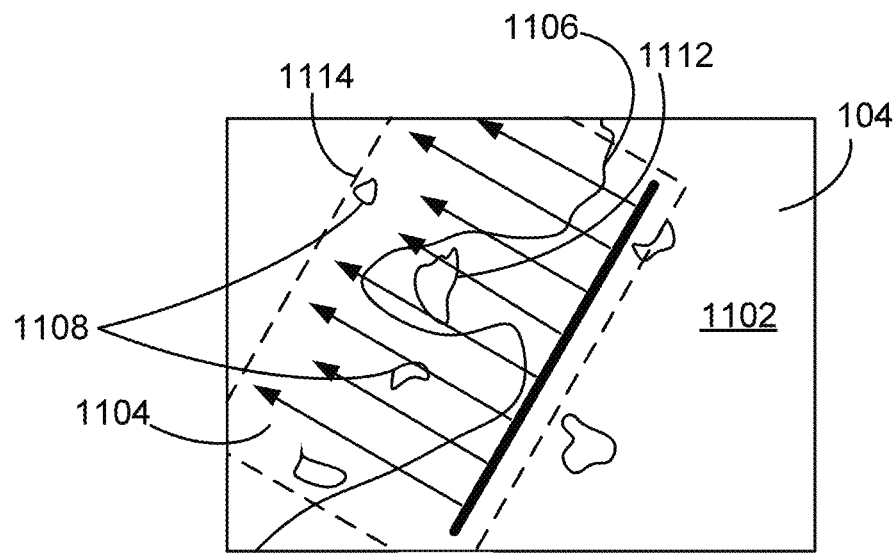
FIGS. 11A and 11B are planar view simplified illustrations of heat distribution over a portion of a surface of tissue in accordance with some embodiments of the invention.
Figure 11B:
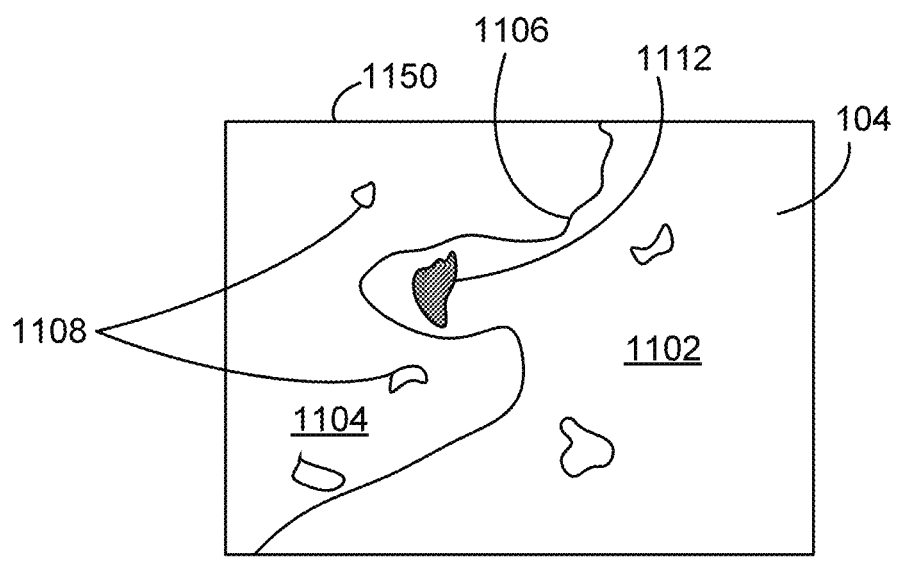

One example for use of vector heating is in tissue border analysis as shown in FIGS. 11A and 11B, which are planar view simplified illustrations of heat distribution over a portion of a surface of tissue in accordance with some embodiments of the invention. In the exemplary embodiment shown in FIG. 11A, surface of tissue 104 comprises two bordering areas 1102 and 1104 separated by a borderline 1106 and appearing to comprise different tissue states e.g., one or more blemishes 1108 or tissue types.

As shown in the exemplary embodiment depicted in FIG. 11A surface of tissue 104 is heated along line 1110 disposed generally on the border 1106 between areas 1102 and 1104 to one side of a suspected blemish 1112. For clarity of explanation, heat distribution from line 902 in a direction away from the suspected blemish is ignored.

To increase resolution and accuracy of the aberrant cell identification, the FOV of imager 108 is limited to area 1114 of surface of tissue 104. Thermal imaging system 100 processor 110 is configured to obtain thermal values from pixel arrays imaging the FOV of imager 108 and process the obtained values as explained elsewhere herein. In some embodiments and as shown in the exemplary embodiment depicted in FIG. 11B, thermal imaging system 100 processor 110 generates a map 1150 identifying tissue segment 1112 as aberrant tissue (e.g., cancerous tissue) by marking tissue segment 1112 by an identifying color or outline within surface of tissue 104 bordering areas 1102 and 1104 as normal.

Random Spot Heating

Figure 12:
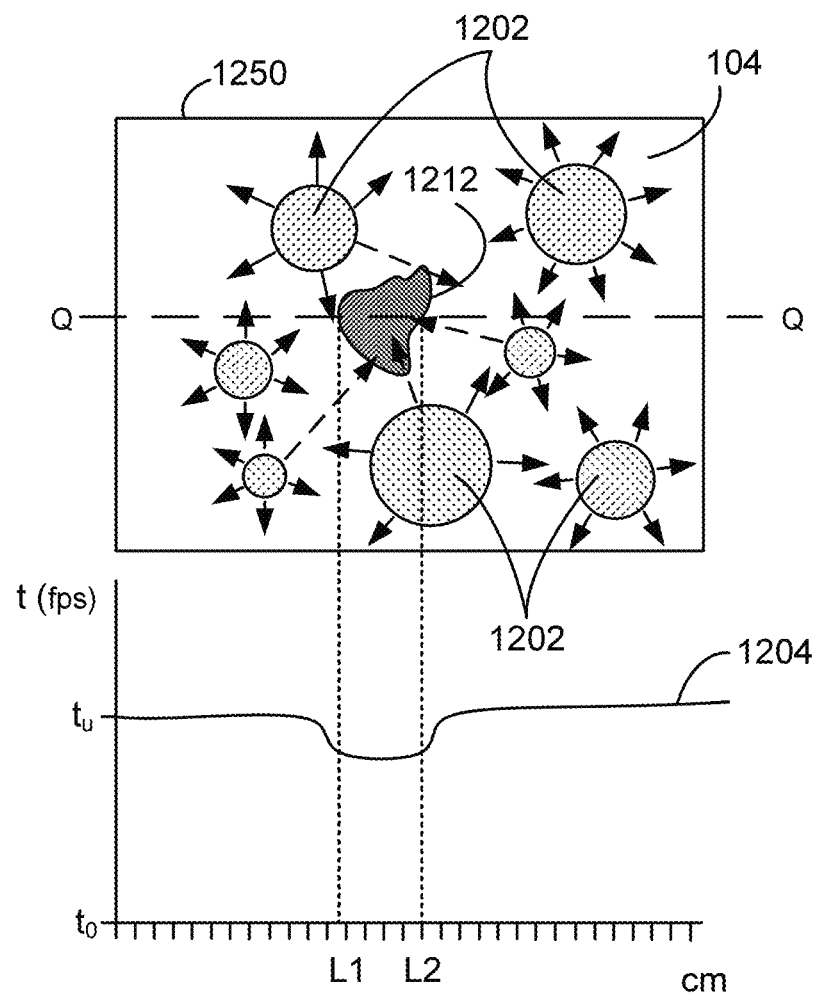
FIG. 12 is a graph and a planar view simplified illustration of heat distribution over a portion of a surface of tissue in accordance with some embodiments of the invention.

Reference is now made to FIG. 12, which is a graph and a planar view simplified illustration of heat distribution over a portion of a surface of tissue in accordance with some embodiments of the invention. In some embodiments and as shown in FIG. 12, a source of heat 102 heats randomly-sized portions 1202 of a surface of tissue 104. In some embodiments, randomly-sized portions 1202 are heated and concurrently and uniformly, e.g., by application of a same level of heat (e.g., Joules) during equal periods of time and the consecutive thermal images at given time intervals are taken by thermal imaging system 100 imager 108.

In some embodiments, and as explained elsewhere herein, thermal imaging system 100 processor 110 processes the obtained images to identify and delineate a tissue segment 1212. For example, in some embodiments, processor 110 is configured to process and identify a time to temperature uniformity ($t_u$) end point at which a majority (Mc %) of the surface of tissue 104 is imaged to be at the same temperature. In some embodiments, a majority (Mc %) of the tissue of surface of tissue 104 is defined by a percentage of the area of surface of tissue 104 within the FOV of imager 108, for example (Mc %) is over 50%, between 50%-99%, 60%-90% and 70%-80%. In some embodiments, processor 110 generates a thermal map 1250 at the end-point ($t_u$) identifying aberrant tissue segment 1212.

The exemplary graph depicted in FIG. 12 shows a curve 1204 of level of temperature at ($t_u$) along an arbitrary line Q-Q over surface of tissue 104. As shown in FIG. 12, graph 1204 exhibits a generally uniform temperature of tissue along line Q-Q except for a length between L1 and L2 at which the temperature is lower. In some embodiments, the lower temperature attained by tissue along portion L1-L2 of line Q-Q may indicate that the tissue comprises a slower growth portion of the thermal curve as explained in detail elsewhere herein identifying the tissue to be aberrant cells. In some embodiments and as described elsewhere herein, thermal imager 100 processor 110 processes consecutive thermal images of the aberrant tissue in portion L1-L2 of line Q-Q and process growth portion of a thermal graph and identify type of aberrant tissue (e.g., cancerous cells).

Figure 13:
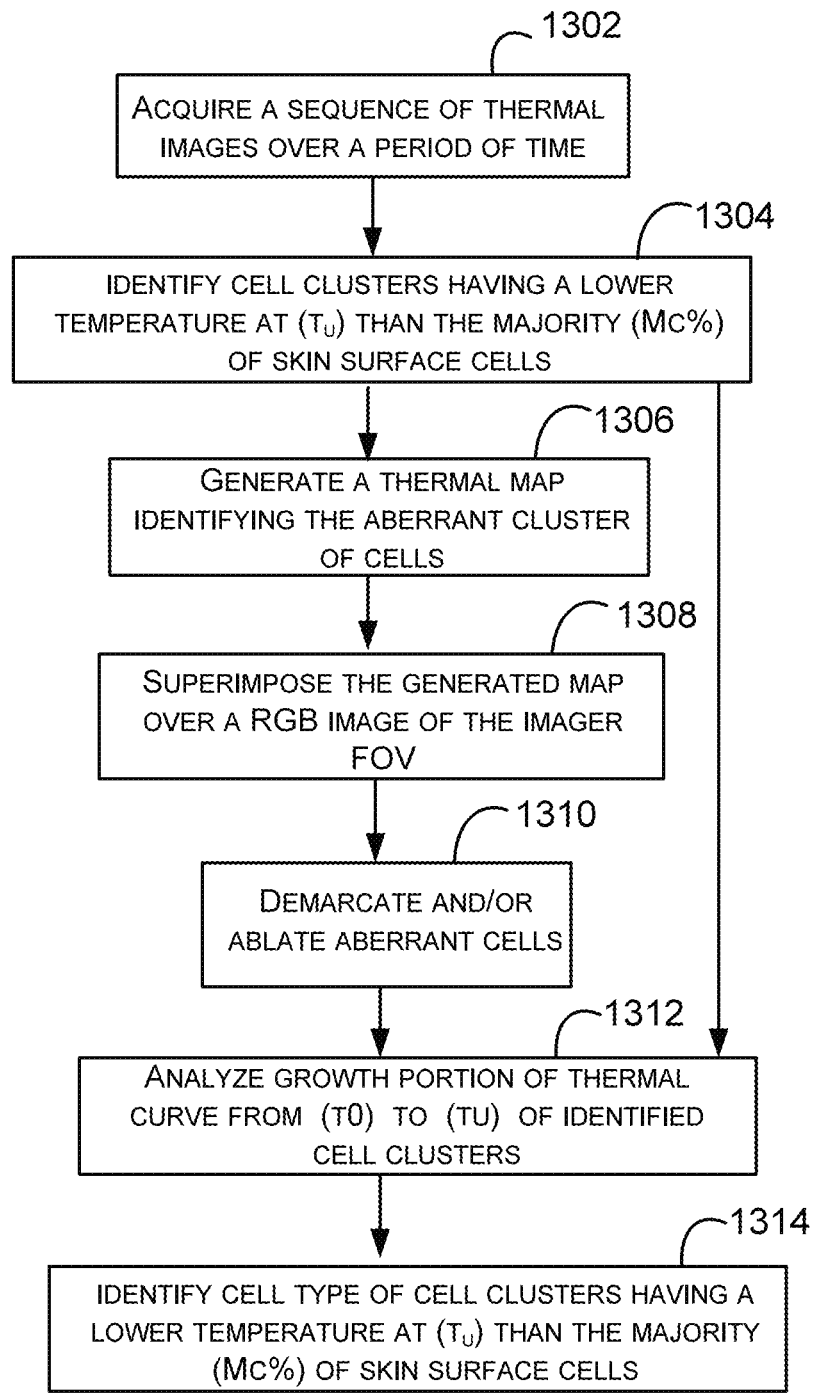
FIG. 13 is an exemplary simplified flow chart illustrating operation of thermal imaging system processor in accordance with some embodiments of the invention.

As depicted in FIG. 13, which is an exemplary simplified flow chart illustrating operation of thermal imaging system 100 processor 110 in accordance with some embodiments of the invention, processor 110 is configured to obtain at 1302 thermal images from imager 108 taken over a period of time from ($t_0$) to ($t_u$) and identifies at 1304 cell clusters (e.g., tissue segment 1212) having a lower temperature at ($t_u$) than the majority (Mc %) of tissue of surface of tissue 104. At 1306, processor generates a thermal map of surface of tissue 104 within the FOV of imager 108 identifying or delineating the cluster of aberrant tissue segment 1212. In some embodiments and optionally, at 1308, processor 110 superimposes the map generated at 1306 on a RGB image of surface of tissue 104 and at 1310 demarcates or ablates the aberrant tissue 112.

In some embodiments and at 1312, processor 110 is configured to process a growth portion of thermal curves of cell cluster identified at 1304 and at 1314 identifies tissue type or state (e.g., cancerous) of tissue segment 1212 having a lower temperature at ($t_u$) than the majority (Mc %) of surface of tissue 104.

Pulsed Heat Application

Figure 14A:
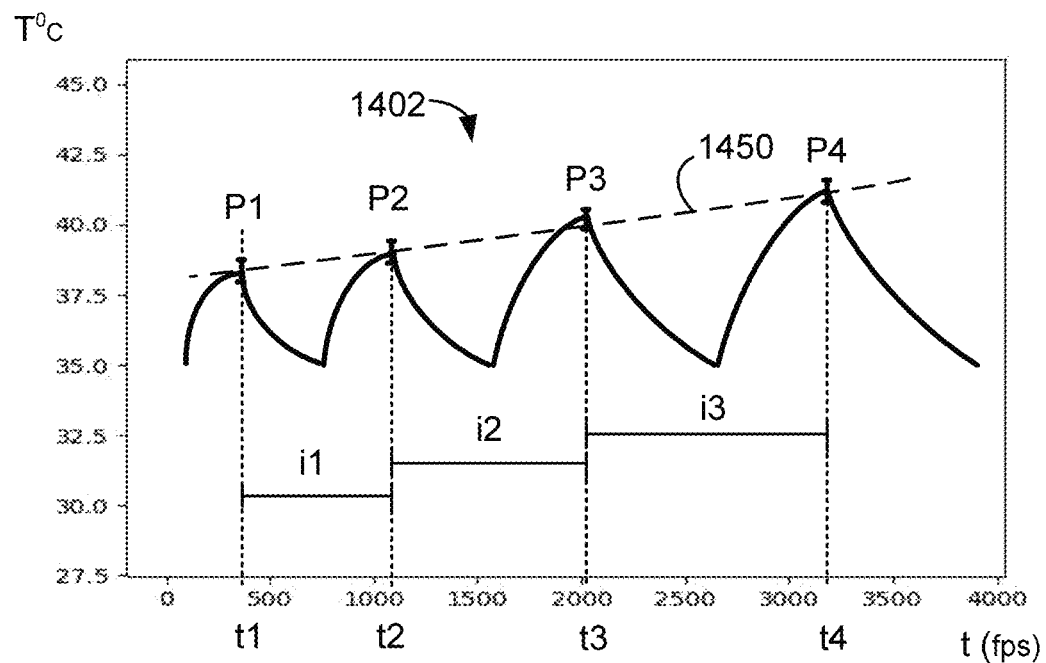
FIGS. 14A and 14B are graphs of thermal curves associated with biothermal behavior of heated cells in accordance with some embodiments of the invention.
Figure 14B:
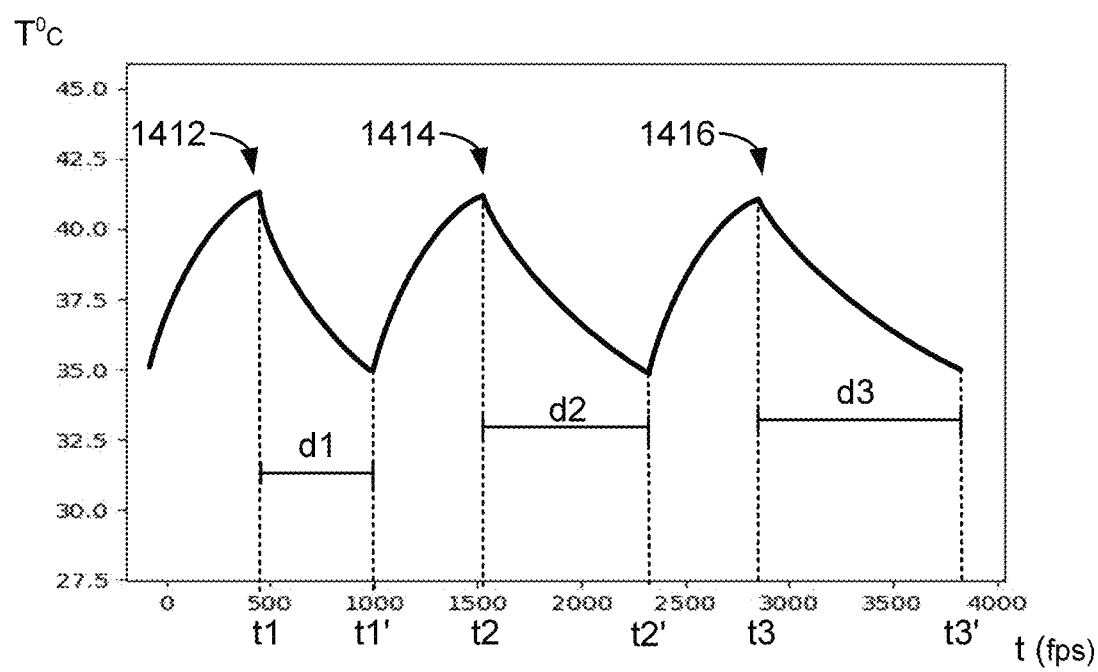

In some embodiments and as shown in FIGS. 14A and 14B, which are graphs of thermal curves associated with biothermal behavior of heated tissue in accordance with some embodiments of the invention, surface of tissue 104 is heated by a plurality of pulses of heat over a period of time. In some embodiments, the heat pulses are applied consecutively and uniformly, e.g., by application of a same level of heat (e.g., Joules) during equal periods of time at equal intervals between heating pulses. Thermal imaging system 100 processor 110 is configured to obtain a plurality of consecutive thermal images from imager 108 and process the thermal behavior of the tissue of surface of tissue 104 in response to the heating pulses.

In some embodiments, shown in FIGS. 14A and 14B and explained in greater detail elsewhere herein, different states or types of tissue exhibit different thermal behavior in response to applied pulsed heat, which is expressed by a variance in thermal graphs associated with the thermal behavior. In one example, shown in FIG. 14A, thermal parameters obtained from imaged tissue exposed over a period of time to pulsed heat and processed by thermal imaging system processor 110 exhibit a curve 1402 comprising one or more growth portions 1404, each followed by one or more decaying portions 1406 and a plurality of temperature peak points 1408.

In some embodiments, processor 110 is configured to perform a top analysis on curve 1402 and based on the analysis to identify a thermal signature specific to a tissue type or state imaged within an FOVp of a pixel, e.g., by identifying temperature peaks e.g., P1, P2, P3 and P4 of consecutive curves in response to consecutive heat pulses at given times e.g., t1, t2, t3 and t4 and processing the relationship between the peaks e.g., time intervals between the peaks e.g., i1, i2, i3 and i4 or a growing linear regression 1450 of the calculated peaks.

In some embodiments, thermal imaging system 100 processor 110 is configured to execute a comparative analysis on selected portions only of the thermal curve e.g., a growth portion, a decay portion and/or a peak temperature at the meeting point of the growth portion and the decay portion e.g., the exemplary graph shown in FIG. 14B, exhibits a growing decay periods d1 between t1 and t1', d2 between t2 and t2' and d3 between t3 and t3' of curves 1412, 1414 and 1416 in response to consecutive heat pulses. In some embodiments, processor 110 is configured, based on the analysis to identify a thermal signature specific to a tissue type or state imaged within an FOVp of a pixel, e.g., by identifying a thermal behavior pattern specific to a tissue type or state.

Fractional Heating

Figure 15:
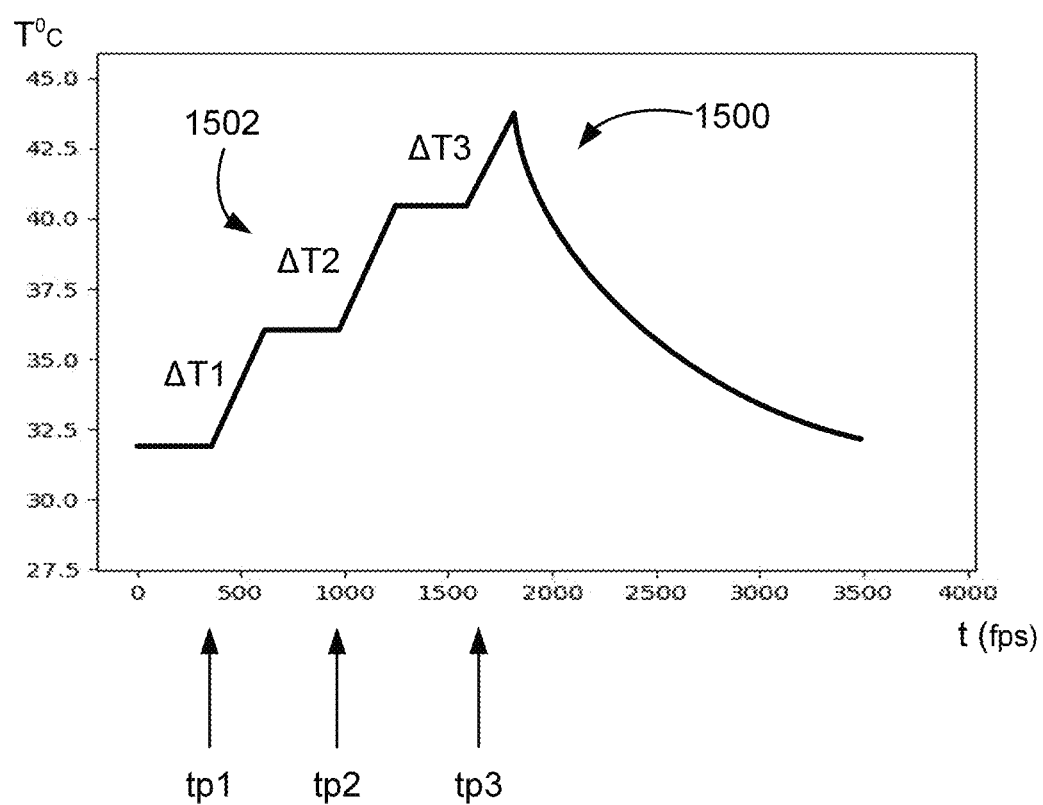
FIG. 15 is a graph of a thermal curve associated with biothermal behavior of heated cells in accordance with some embodiments of the invention.

In some embodiments and as shown in FIG. 15, which is a graph of a thermal curve associated with biothermal behavior of heated tissue in accordance with some embodiments of the invention, surface of tissue 104 is heated fractionally. In some embodiments, heat is applied by a plurality of pulses of set (e.g., same level of heat or Joules) at predetermined intervals, e.g., equal or varying in length and thermal imaging system 100 imager 108 obtains consecutive thermal images throughout the growth portion 1502 of the obtained thermal curve 1500.

In the exemplary embodiment depicted in FIG. 15, three heat pulses are applied at three points in time—tP1, tP2 and tP3 resulting in a stepped growth portion 1502 of curve 1500 having three fractions ΔT1, ΔT2 and ΔT3. A potential advantage of fractional heating is in that the analysis is carried out on fractions of growth portion 1502 rather than on the full growth portion 1500 allowing for increased resolution and accuracy of the aberrant cell identification. In some embodiments, variance between tissue states or types is expressed in variances within only one fraction of fractions ΔT1, ΔT2 and ΔT3 providing a higher resolution of a tissue-type signature pattern and increasing the accuracy and specificity of the tissue type or state identification.

3D Heating

Figure 16A:
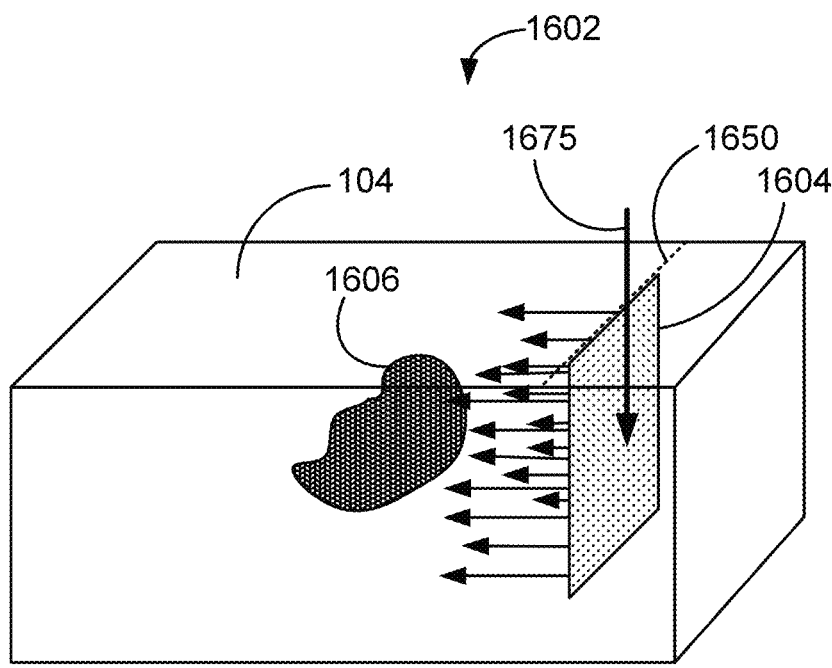
FIGS. 16A and 16B are sectional view simplified illustrations of heat distribution inside a portion of a surface of tissue in accordance with some embodiments of the invention.
Figure 16B:
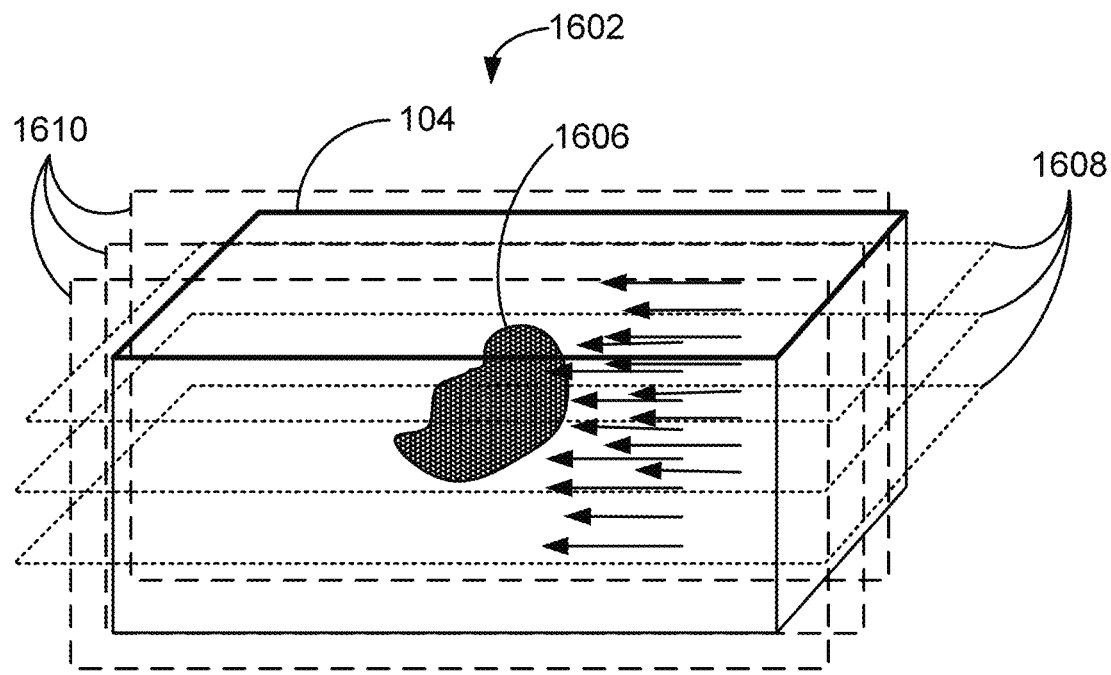

Reference is now made to FIGS. 16A and 16B, which are sectional view simplified illustrations of heat distribution inside a portion of a surface of tissue in accordance with some embodiments of the invention. In some embodiments, a volume of tissue 1602 under surface of tissue 104 is heated along a plane 1604 using three-dimensional heating systems such as Ultrasound, Laser, IR or RF radiation applied at varying frequencies along a line 1650 disposed to one side of a suspected aberrant tissue 1606 in a direction from the surface into deeper tissue indicated by an arrow 1675.

As shown in FIGS. 16A and 16B heat distribution inside a portion 1602 under surface of tissue 104 occurs along lines 1608. For clarity of explanation, heat distribution from plane 1604 in a direction away from the suspected tissue segment 1606 is ignored.

In some embodiments, imaging system 100 processor 110 is configured to process and process a plurality of thermal images taken by a 3D thermal imaging system e.g., MM, CT Scanner, Ultrasound transceiver, RF transceiver or similar, concurrently or consecutively along one or more planes at varying spatial orientation in respect to surface of tissue 104. In the exemplary embodiment illustrated in FIG. 16, a plurality of thermal images taken by a 3D thermal imaging system, concurrently or consecutively are taken along a plurality planes spatially orientated parallel (planes 1608) and/or perpendicular (planes 1610) in respect to surface of tissue 104.

As shown in FIG. 16B and in some embodiments, thermal imaging system 100 processor 110 is configured to compile the thermal behavior values obtained from thermal images taken along plurality of planes 1608 and/or planes 1610 and as explained in greater detail elsewhere herein, extract information regarding one or more physiological or pathological thermal parameters associated with tissue identified as aberrant tissue cells 1606 in one or more obtained thermal images and generate at least a three-dimensional outline of suspected aberrant tissue 1606.

In some embodiments, the duplicity of at least part of the values obtained by thermal imaging system 100 processor 110 and comparison between obtained values from the obtained images increases accuracy and specificity of the tissue type identification and location inside tissue under surface of tissue 104. In some embodiments, thermal imaging system 100 processor 110 is configured to superimpose the 3D outline of suspected aberrant tissue 1606 onto a RGB 3D image of tissue under surface of tissue 104 to assist the health professional clearly and accurately identify the borders of suspicious cell cluster 904 within the tissue.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

In the description and claims of the application, each of the words "comprise" "include" and "have", and forms thereof, are not necessarily limited to members in a list with which the words may be associated. In addition, where there are inconsistencies between this application and any document incorporated by reference, it is hereby intended that the present application controls.

Methods and computer program products are disclosed herein that may automatically construct (i.e., without human intervention) a list of relevant claims and supportive evidence given a topic under consideration (TUC). Thus, for example, one may extract persuasive claims supporting his or her point of view as well as be prepared for counter claims which the other side may raise while discussing the TUC.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method comprising:
controlling a heating source to heat at least a surface of at least a portion of a tissue, from an initial, base temperature over a predetermined first period of time;
receiving thermal data associated with the tissue, wherein said thermal data is sampled over the first period of time and over a second period of time at which the tissue is allowed to passively return to the base temperature;
deriving from said thermal data a set of thermal distribution related features with respect to each of a plurality of locations within said tissue, wherein the set of features comprises calculating features for the first period of time and the second period of time;
segmenting said tissue into segments, each comprising one or more of said plurality of locations having corresponding sets of features; and
generating an output, based on said sets of features, comprising at least one of, indicating said tissue segments, and identifying various tissue states in said tissue segments.

2. The method according to claim 1, wherein said thermal data is received from at least one of thermal imaging, infrared (IR) sensor, mercury thermometer, resistance thermometer, thermistor, thermocouple, semiconductor-based temperature sensor, pyrometer, gas thermometer, laser thermometer and ultrasound.

3. The method according to claim 2, wherein said thermal data is received by thermal imaging, and wherein each of said locations comprises a pixel or a voxel of an image.

4. The method according to claim 1, wherein said set of features represents at least one of: tissue organism metabolic heat source, heat loss due to blood perfusion, blood temperature, tissue density, specific heat, tissue thermal conductivity factor, tissue thermal conductivity coefficient, tissue thermal conductivity surface area, tissue surface temperature, time-dependent thermal gradient between tissue and ambient temperature, ambient temperature, and a heat source temperature.

5. The method according to claim 1, wherein said correspondence is determined, based, at least in part, on a variance value of all of said features not exceeding a specified threshold.

6. The method according to claim 1, further comprising determining a tissue state or type associated with each of said segments, based, at least in part, on correlating said set of features associated with each of said segments with predefined values associated with a plurality of tissue states or types.

7. The method according to claim 6, wherein said determining is performed by a machine learning classifier trained, at a training stage, on a training set comprising:
(i) a plurality of sets of features, each derived from thermal data sampled at each of a plurality of locations within a plurality of tissues, while said tissues are being thermally disturbed; and
(ii) labels associated with a state or type of each of said locations.

8. The method of claim 7, further comprising applying, at an inference stage, said trained machine learning classifier to target a set of features derived from thermal data sampled at a location of a tissue, while said tissue is being thermally disturbed, to determine a state or type of said location.

9. A computer program product comprising a non-transitory computer-readable storage medium having program code embodied therewith, the program code executable by at least one hardware processor to:
control a heating source to heat at least a surface of at least a portion of a tissue, from an initial, base temperature over a predetermined first period of time;
receive thermal data associated with the tissue, wherein said thermal data is sampled over the first period of time and over a second period of time at which the tissue is allowed to passively return to the base temperature;
derive from said thermal data a set of thermal distribution related features with respect to each of a plurality of locations within said tissue, wherein the set of features comprises calculating features for the first period of time and the second period of time;
segment said tissue into segments, each comprising one or more of said plurality of locations having corresponding sets of features; and
generate an output, based on said sets of features, comprising at least one of, indicating said tissue segments, and identifying various tissue states in said tissue segments.

10. The computer program product according to claim 9, wherein said thermal data is received from at least one of thermal imaging, infrared (IR) sensor, mercury thermometer, resistance thermometer, thermistor, thermocouple, semiconductor-based temperature sensor, pyrometer, gas thermometer, laser thermometer and ultrasound.

11. The computer program product according to claim 10, wherein said thermal data is received by thermal imaging and wherein each of said locations comprises a pixel or a voxel.

12. The computer program product according to claim 9, wherein said set of features represents at least one of: tissue organism metabolic heat source, heat loss due to blood perfusion, blood temperature, tissue density, specific heat, tissue thermal conductivity factor, tissue thermal conductivity coefficient, tissue thermal conductivity surface area, tissue surface temperature, time-dependent thermal gradient between tissue and ambient temperature, ambient temperature, and a heat source temperature.

13. The computer program product according to claim 9, wherein said correspondence is determined, based at least in part on a variance value of all said variables and said features not exceeding a specified threshold.

14. A system, comprising:
a thermal sensor configured to sample thermal data from a tissue, while said tissue is being thermally disturbed;
a heating source; and
a processor configured to:
control said heating source to heat at least a surface of at least a portion of the tissue, from an initial, base temperature over a predetermined first period of time;
receive thermal data associated with the tissue, wherein said thermal data is sampled over the first period of time and over a second period of time at which the tissue is allowed to passively return to the base temperature;
derive from said thermal data a set of thermal distribution related features associated with each of a plurality of locations within said tissue, wherein the set of features comprises calculating features for the first period of time and the second period of time;
segment said tissue into segments, each comprising one or more of said plurality of locations having corresponding sets of features; and
generate an output, based on said sets of features, comprising at least one of indicating said tissue segments, and identifying various tissue states in said tissue segments.

15. The system according to claim 14, wherein said thermal data is received from at least one of thermal imaging, infrared (IR) sensor, mercury thermometer, resistance thermometer, thermistor, thermocouple, semiconductor-based temperature sensor, pyrometer, gas thermometer, laser thermometer and ultrasound.

16. The system according to claim 15, wherein said thermal data is received by thermal imaging and wherein each of said locations comprises a pixel or a voxel.

17. The system according to claim 14, wherein said set of features represents at least one of: tissue organism metabolic heat source, heat loss due to blood perfusion, blood temperature, tissue density, specific heat, tissue thermal conductivity factor, tissue thermal conductivity coefficient, tissue thermal conductivity surface area, tissue surface temperature, time-dependent thermal gradient between tissue and ambient temperature, ambient temperature, and a heat source temperature.

* * * * *